United States Patent [19]

Fabre et al.

[11] Patent Number: 4,684,658
[45] Date of Patent: Aug. 4, 1987

[54] ANTI-THROMBOTIC ORTHO-CONDENSED PYRROLE DERIVATIVES, COMPOSITIONS, AND METHOD OF USE THEREFOR

[75] Inventors: Jean-Louis Fabre, Paris; Daniel Farge, Thiais; Claude James; Daniel Lavé, both of Paris, all of France

[73] Assignee: Rhone-Poulenc Sante, Courbevoie, France

[21] Appl. No.: 684,061

[22] Filed: Dec. 20, 1984

[30] Foreign Application Priority Data

Dec. 21, 1983 [FR] France .................... 83 20474

[51] Int. Cl.$^4$ ............ A61K 31/38; C07D 513/04; C07D 417/14
[52] U.S. Cl. ........................... 514/338; 514/226; 514/232; 514/239; 514/300; 514/337; 514/339; 514/365; 514/367; 514/368; 514/375; 514/413; 544/3; 544/47; 544/90; 544/270; 546/246; 546/270; 546/271; 548/146; 548/152; 548/179; 548/180; 548/193; 548/215; 548/217; 548/452
[58] Field of Search ............ 544/47, 90, 270, 3; 514/222, 226, 232, 239, 338; 546/270, 271

[56] References Cited

PUBLICATIONS

Benages et al, J.O.C. 43(22), 1978, pp. 4273-4276.

Primary Examiner—John M. Ford
Assistant Examiner—J. G. Mullins
Attorney, Agent, or Firm—Stevens, Davis, Miller & Mosher

[57] ABSTRACT

The invention provides novel pyrrole derivatives of formula:

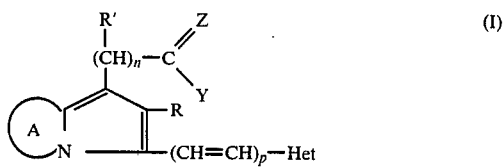

(I)

in which $R'=H$, alkyl or phenyl optionally substituted by halogen, alkyl, alkyloxy or alkylthio, $Z=O$ or S, $p=0$ or 1, and either A is a heterocyclic ring such that it forms, with pyrrole, a 1H,3H-pyrrolo[1,2-c]thiazole, 2,3-dihydro-1H-pyrrolizine optionally substituted by OH, 5,6,7,8-tetrahydroindolizine, 1,2-dihydro-4H-pyrrolo[1,2-c]-1,3-thiazine, 2,3-dihydropyrrolo[2,1-b]thiazole, 1H,3H-pyrrolo[1,2-c]oxazole, 1,2-dihydro-4H-pyrrolo]1,2-c]-1,3-oxazine or 2,3-dihydropyrrolo[2,1-b]oxazole ring system, $n=0$ or 1, Het=3-pyridyl or 5-thiazolyl, and (1) either $R=H$, halogen, alkyl or phenyl optionally substituted by halogen, alkyloxy or alkylthio and $Y=$ alkyl or phenyl optionally substituted by halogen, alkyl, alkyloxy or alkylthio, or $Y=-NR_1R_2$ with:
either $R_1=H$ and $R_2=$ unsubstituted alkyl, cycloalkyl ($C_3$-$C_6$), alkenyl ($C_2$-$C_4$), alkynyl ($C_3$-$C_4$), benzyl or phenyl radicals optionally substituted by halogen, alkyl, alkyloxy, alkylthio, $CF_3$ or $NO_2$, or $R_2=$ adamantyl, pyridyl or pyridylmethyl, or $R_1$ and $R_2=$ both unsubstituted alkyl or $R_1$ and $R_2$ from a 4-phenylpiperazin-1-yl radical the phenyl part of which may be substituted by halogen, alkyl, alkyloxy, alkylthio, $CF_3$ or $NO_2$ (2) or $R=$ halogen, alkyl or phenyl optionally substituted by halogen, alkyloxy or alkylthio, and $Y=NH_2$ or A is a heterocyclic ring such that it forms, with pyrrole, a 2,3-dihydro-1H-pyrrolizine substituted by OH, 2,3-dihydropyrrolo[2,1-b]thiazole or 2,3-dihydropyrrolo[2,1-b]oxazole ring system, $R=H$, $Y=NH_2$, $n=0$ or 1 or Het=5-thiazolyl or 3-pyridyl, or A is a heterocyclic ring such that it forms, with pyrrole, a 1H,3H-pyrrolo[1,2-c]thiazole, 2,3-dihydro-1H-pyrrolizine, 5,6,7,8-tetrahydroindolizine, 1,2-dihydro-4H-pyrrolo[1,2-c]-1,3-thiazine, 1H,3H-pyrrolo[1,2-c]oxazole or 1,2-dihydro-4H-pyrrolo[1,2-c]-1,3-oxazine ring system, $R=H$, $Y=NH_2$ and either Het=5-thiazolyl and $n=0$ or 1 or Het=3-pyridyl and $n=1$, the alkyl containing 1 to 4 C as a straight or branched chain, and their acid addition salts, pharmaceutical compositions containing the said pyrrole derivatives and process for their preparation. These pyrrole derivatives are useful in prophylactic and therapeutic treatment of thrombotic complaints.

17 Claims, No Drawings

ANTI-THROMBOTIC ORTHO-CONDENSED PYRROLE DERIVATIVES, COMPOSITIONS, AND METHOD OF USE THEREFOR

The present invention provides new ortho-condensed pyrrole derivatives of formula:

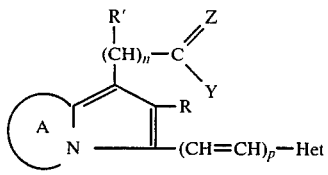

in which R' denotes a hydrogen atom or an alkyl or phenyl radical which is unsubstituted or substituted by halogen, alkyl, alkyloxy or alkylthio, Z denotes an oxygen or sulphur atom, p denotes zero or 1; and (A) either the symbol A denotes a heterocyclic ring which, with the pyrrole nucleus with which it is condensed, forms a ring system selected from 1H,3H-pyrrolo[1,2-c]thiazole, 2,3 dihydro-1H-pyrrolizine unsubstituted or substituted by hydroxy, 5,6,7,8-tetrahydroindolizine, 1,2-dihydro-4H-pyrrolo[1,2-c]-1,3-thiazine, 2,3-dihydropyrrolo[2,1-b] thiazole, 1H,3H-pyrrolo[1,2-c] oxazole, 1,2-dihydro-4H-pyrrolo[1,2-c]-1,3-oxazine and 2,3-dihydropyrrolo[2,1-b] oxazole, n denotes 0 or 1, Het denotes 3-pyridyl or 5-thiazolyl, and (1) either R denotes hydrogen or halogen or an alkyl or phenyl radical which is unsubstituted or substituted by halogen, alkyl, alkyloxy or alkylthio, and Y denotes an alkyl (preferably methyl) or phenyl radical which is unsubstituted or substituted by halogen, an alkyl, alkyloxy or alkylthio radical, or Y denotes a radical of formula:

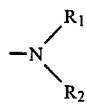

in which either $R_1$ denotes a hydrogen atom and $R_2$ denotes an unsubstituted alkyl radical, a cycloalkyl radical of 3 to 6 carbon atoms, an alkenyl radical of 2 to 4 carbon atoms, an alkynyl radical of 3 or 4 carbon atoms, or a benzyl or phenyl radical which is unsubstituted or substituted by halogen, alkyl, alkyloxy, alkythio, trifluoromethyl or nitro, or $R_2$ denotes an adamantyl, pyridyl or pyridylmethyl radical; or $R_1$ and $R_2$ both denote an unsubstituted alkyl radical, or $R_1$ and $R_2$ form, with the nitrogen atom to which they are attaohed, a 4-phenylpiperazin-1-yl radical, the phenyl part of which is unsubstituted or substituted by halogen, alkyl, alkyloxy, alkylthio, trifluoromethyl or nitro;

(2) or R denotes halogen or an alkyl or phenyl radical which is unsubstituted or substituted by halogen, alkyl, alkyloxy or alkylthio, and Y denotes an amino radical;

(B) or the symbol A denotes a heterocyclic ring which, with the pyrrole ring with which it is condensed, forms a ring system selected from 2,3-dihydro-1H-pyrrolizine substituted by a hydroxy radical, 2,3-dihydropyrrolo[2,1-b]thiazole or 2,3-dihydropyrrolo[2,1-b]oxazole, R denotes a hydrogen atom, Y denotes an amino radical, n denotes zero or 1, and Het denotes 5-thiazolyl or 3-pyridyl, (C) or the symbol A denotes a heterocyclic ring which, with the pyrrole nucleus with which it is condensed, forms a ring system selected from 1H,3H-pyrrolo[1,2-c]thiazole, 2,3-dihydro-1H-pyrrolizine, 5,6,7,8-tetrahydroindolizine, 1,2-dihydro-4H-pyrrolo[1,2-c]-1,3-thiazine, 1H,3H-pyrrolo[1,2-c] oxazole and 1,2-dihydro-4H-pyrrolo[1,2-c]-1,3-oxazine ring system, R denotes a hydrogen atom, Y denotes an amino radical; and either Het denotes 5-thiazolyl and n is zero or 1, or Het denotes 3-pyridyl and n is 1; it being understood that, unless specially mentioned, the alkyl radicals and alkyl portions contain 1 to 4 carbon atoms each and are straight-chain or branched-chain; and the acid addition salts of the said pyrrole derivatives.

According to the invention, the compounds of formula (I) in which Z denotes an oxygen atom, Y denotes an alkyl or phenyl radical optionally substituted by a halogen atom or an alkyl, alkyloxy or alkylthio radical and the other symbols are defined as previously, may be obtained by reaction of an organomagnesium derivative of formula:

in which Y' denotes an alkyl or phenyl radical which is unsubstituted or substituted by halogen, alkyl, alkyloxy or alkylthio and $X_1$ denotes a halogen atom, with a nitrile of formula:

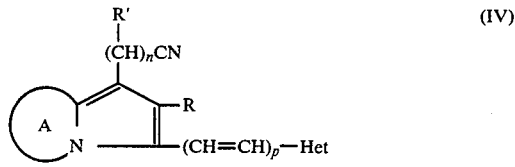

in which the symbols are defined as previously, by proceeding according to the methods known to the person skilled in the art for reacting an organomagnesium derivative with a nitrile.

The nitriles of general formula (IV), in which n is equal to zero and the other symbols are defined as previously, may be obtained by reaction of a nitrile of formula:

in which X denotes a halogen atom such as chlorine or bromine and R is defined as previously, with a product of formula:

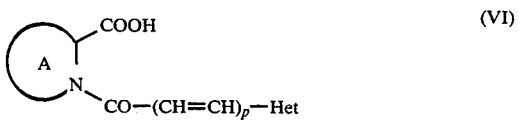

in which the various symbols are defined as previously.

The reaction is generally carried out in acetic anhydride by heating to a temperature of between 80° and 130° C.

The products of general formula (V) may be obtained by applying or adapting the methods described by L. Leclercq and A. Bruylants, Bull. Soc. chim. belges, 58, 5 (1949) or J. C. Pommelet et al., Angew. Chem., 93, 594 (1981), or R. Carrie et al., Bull. Soc. chim. France, 1963 (1976) or H. Brintzinger et al., Angew. Chem., 60, 312 (1948).

The products of general formula (VI) may be obtained by condensing a product of general formula:

  (VII)

$$Het-(CH=CH)_p-COX_2 \quad (VII)$$

which p is defined as previously and $X_2$ denotes a halogen atom or forms with the radical to which it is attached a mixed anhydride, with a product of general formula:

  (VIII)

in which A is defined as previously and $R_o$ denotes a hydrogen atom or an alkyl radical, followed by hydrolysis when $R_o$ denotes an alkyl radical and/or when the symbol A in the general formula (VI) must denote a pyrrolidine substituted by a hydroxy radical.

The condensation of the product of general formula (VII) with the product of general formula (VIII) is generally carried out in an inert organic solvent such as chloroform in the presence of an acid acceptor such as triethylamine at a temperature of between 0° and 65° C.

When $R_o$ denotes an alkyl radical and/or A denotes a pyrrolidine substituted by a hydroxy radical, the hydrolysis is carried out by any method known to the person skilled in the art for converting an ester to acid and/or to alcohol without affecting the remainder of the molecule, particularly by heating in an alkaline medium in water or in an aqueous-alcoholic solvent such as a water-ethanol mixture at a temperature of between 20° and 80° C.

The products of general formula (VIII) may be obtained by applying or adapting methods described by J. C. Wriston and C. G. McKenzie, J. Biol. Chem., 225, 607 (1957) or S. Wolff, G. Militello et al., Tet. Letters, 3913 (1979) or R. L. Johnson, E. E. Smissman and N. P. Plotnikoff, J. Med. Chem., 21, 165 (1978).

When A denotes a heterocyclic ring containing an oxygen atom, the product of general formula (VIII) is not isolated but the product of general formula (VI) is obtained directly, since the condensation of the product of general formula (VII) takes place in situ in the reaction medium.

The nitriles of general formula (IV) in which n is equal to 1 and the other symbols are defined as previously may be obtained by condensing tosylmethyl isocyanide of formula:

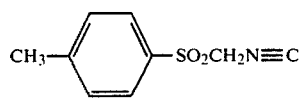  (IX)

with a carbonylated derivative of general formula:

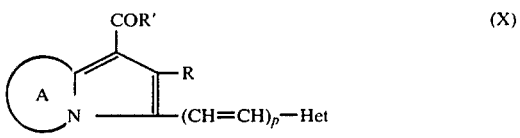  (X)

in which the symbols are defined as previously.

The condensation is generally carried out in two successive steps: (a) by operating in a solvent such as 1,2-dimethoxyethane, dimethyl sulphoxide or hexamethylphosphoramide in the presence of a base such as potassium tert-butylate at a temperature of between −60° C. and 0° C., and then (b) by continuing the reaction at a temperature between 0° C. and the reflux temperature of the reaction mixture after having added an alcohol such as methanol.

The carbonylated derivatives of general formula (X) may be prepared by reaction of a product of general formula:

  (XI)

in which R and R' are defined as previously and $X_3$ denotes a halogen atom such as chlorine or bromine, with a product of general formula (VI) such as defined previously.

The operation is generally carried out in acetic anhydride at a temperature of between 80° and 130° C.

The products of general formula (XI) may be prepared by applying or adapting the methods described by H. Schulz and H. Wagner, Angew. Chem., 62, 105 (1950) or H. Hibbert, E. O. Houghton and K. A. Taylor, J. Amer. Chem. Soc., 51, 611 (1929).

The carbonylated derivatives of general formula (X) in which A is defined as previously, p is equal to 0 and R' denotes a hydrogen atom may also be prepared by formylation of a product of general formula:

  (XII)

in which A, R and Het are defined as previously.

The formylation is generally carried out by any means known to the person skilled in the art for formylating a pyrrole nucleus without affecting the remainder of the molecule, particularly by means of a mixture of phosphoryl chloride and dimethylformamide, at a temperature of between 0° and 20° C.

The products of general formula (XII) may be prepared by decarboxylation of an acid of general formula:

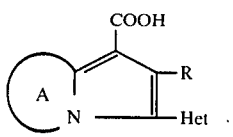 (XIII)

in which A, Het and R are defined as previously, according to the methods known in themselves for decarboxylating an acid, for example by heating in the presence of copper powder.

The acids of general formula (XIII) may be prepared by hydrolysis of the nitriles of general formula (IV) in which p and n denote the number zero and the other symbols are defined as previously.

The hydrolysis of the nitriles of general formula (IV) may be carried out by any method known to the person skilled in the art for converting a nitrile to acid without affecting the remainder of the molecule. It is generally advantageous to carry out the hydrolysis in a basic medium in a high-boiling alcohol, for example by means of potassium hydroxide in ethylene glycol between 100° C. and the reflux temperature of the reaction medium.

According to the invention, the products of general formula (I) in which the symbols are defined as previously, with the exception in the case of Z denoting a sulphur atom and in the case of Y denoting an alkyl or phenyl radical optionally substituted by a halogen atom or an alkyl, alkyloxy or alkylthio radical, may be prepared by reaction of ammonia or an amine of general formula:

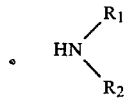 (XIV)

in which $R_1$ and $R_2$ are defined as previously, with an acid of general formula:

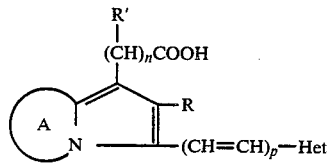 (XV)

in which the various symbols are defined as previously.

It is particularly advantageous to employ the acid of general formula (XV) in an activated form such as the acid chloride or to react it with N,N'-carbonyldiimidazole or an alkyl chloroformate before reaction with ammonia or the amine of general formula (XIV).

It is generally preferable to employ the acid chloride and to carry out the reaction in an organic solvent such as chloroform or methylene chloride at a temperature between 0° C. and the reflux temperature of the reaction mixture.

The acids of general formula (XV) may be prepared by hydrolysis of the nitriles of general formula (IV) in which the various symbols are defined as previously. The hydrolysis of the nitriles of general formula (IV) may be carried out by any method known to the person skilled in the art for converting a nitrile to acid without affecting the remainder of the molecule. It is generally advantageous to carry out the hydrolysis in a basic medium in a high-boiling alcohol, for example by means of potassium hydroxide in ethylene glycol between 100° C. and the reflux temperature of the reaction medium.

The acids of general formula (XV) in which R denotes a halogen atom, p is equal to 0 and the other symbols are defined as previously may also be obtained by halogenation of a product of general formula (XV) in which R denotes a hydrogen atom, p is equal to 0 and the other symbols are defined as previously, by carrying out the operation by any method known to the person skilled in the art, which makes it possible to carry out the required reaction without affecting the remainder of the molecule.

According to the invention, the products of general formula (I) in which Z denotes an oxygen atom, Y denotes a methyl radical and the other symbols are defined as previously, may be obtained by reaction of the ethoxymagnesium derivative of ethyl malonate with an acid halide of general formula:

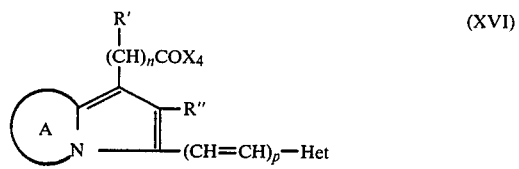 (XVI)

in which $X_4$ denotes a halogen atom, R" has the definition given previously for R and the other symbols are defined as previously, by carrying out the operation according to the methods known to the person skilled in the art for reacting the ethoxymagnesium derivative of ethyl malonate with an acid halide.

The products of general formula (XVI) may be obtained from the acids of general formula (XV) defined as previously by any method known to the person skilled in the art for converting an acid to acid halide without affecting the remainder of the molecule.

According to the invention, the products of general formula (I) in which Z denotes a sulphur atom and the other symbols are defined as previously may be prepared by thionation of a product of general formula (I) in which Z denotes an oxygen atom and the other symbols are defined as previously, that is to say a product of general formula:

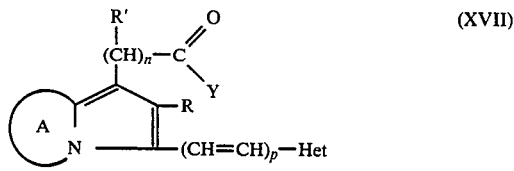 (XVII)

The reaction is generally carried out by means of a thionation reagent such as phosphorus pentasulphide in an organic solvent such as toluene, dioxane or pyridine, at a temperature in the region of 100° C. or by means of LAWESSON's reagent [2,4-bis (4-methoxyphenyl) 2,4 dithioxo-1,3-dithia-2,4 diphosphetane] in an organic solvent such as toluene at a temperature in the region of 50° C. or 1,2- dimethoxyethane or hexamethylphosphoramide at a temperature in the region of 20° C.

According to the invention, the products of general formula (I) in which Z denotes a sulphur atom, Y denotes an amino radical, p is equal to 0 and the other symbols are defined as previously, may be prepared from the nitriles of general formula (IV) in which the symbols have the corresponding definition by any method known to the person skilled in the art for converting a nitrile to a thioamide without affecting the remainder of the molecule. It is particularly advantageous to react the nitrile of general formula (IV) with hydrogen sulphide in a solvent such as pyridine in the presence of triethylamine, by carrying out the operation at a temperature of between 0° and 50° C.

According to the invention, the products of general formula (I) in which the symbols are defined as previously in (A2), in B or in C, may be prepared by hydrolysis of a nitrile of general formula (IV) in which the symbols have the corresponding definitions.

The hydrolysis may be carried out by any means known to the person skilled in the art for converting a nitrile to amide without affecting the remainder of the molecule, particularly by heating in an alkaline medium in an organic solvent such as tert-butanol at a temperature of between 30° and 85° C., or in a concentrated acid medium at a temperature of between 20° and 100° C.

According to the invention, the products of general formula (I) in which Z denotes an oxygen atom, n is equal to zero and the other symbols are defined as previously, may be prepared by reaction of a product of general formula:

R—C≡C—CO—Y         (XVIII)

in which the symbols are defined as previously, with a product of general formula (VI) defined as previously.

The operation is generally carried out in acetic anhydride by heating at a temperature of between 80° and 130° C.

The products of general formula (XVIII) may be prepared by applying or modifying the method described by W. D. Crow and N. J. Leonard, J. Org. Chem., 30, 2660 (1965).

According to the invention, the products of general formula (I) in which R denotes a halogen atom, p is equal to 0 and the other symbols are defined as previously, may also be prepared by halogenation of a product of general formula (I) in which R denotes a hydrogen atom, p is equal to 0 and the other symbols are defined as previously, by employing any method known to the person skilled in the art which makes it possible to carry out the reaction without affecting the remainder of the molecule, for example by reaction with a halogen in a solvent such as acetic acid.

When, in the various procedures described above, some reactions are incompatible with the functions present in the molecule, it is obvious that these functions must first be protected by blocking. The blocking and the subsequent unblocking may be carried out by any method known to the person skilled in the art.

The new products of general formula (I) may be purified by the usual known methods, for example by crystallisation, chromatography, or successive extractions in acid and basic medium.

The new products of general formula (I) may be converted into salts of addition with acids by reaction with an acid in an organic solvent such as an alcohol, a ketone, an ether or a chlorinated solvent. The salt which is formed precipitates, after concentration of its solution if appropriate; it is separated off by filtration or decantation.

The new products of general formula (I) and their salts have interesting pharmacological properties which make them useful in the prophylactic and therapeutic treatment of thrombotic complaints. They have been shown to be active in the mouse at dosages below 100 mg/kg administered orally in the test for generation of serum thromboxane $A_2$ in accordance with the method of R. J. Flower et al. [Brit. J. Pharmacol. 74 (4) 791 P (1981)].

The new products of general formula (I) and their salts show, in addition, low toxicity. Their $LD_{50}$ is generally between 300 and 900 mg/kg, administered orally in the mouse.

For medicinal application, the new products of general formula (I) may be used as such or in the form of pharmaceutically acceptable salts, that is to say salts which are non-toxic in the dosages employed.

As examples of pharmaceutically acceptable salts mention may be made of the salts of addition with inorganic acids such as hydrochlorides, sulphates, nitrates or phosphates, or with organic acids, such as acetates, propionates, succinates, benzoates, fumarates, maleates, methanesulphonates, isethionates, theophylline-acetates, salicylates, phenolphthalinates, methylenebis-β-oxynaphthoates or substituted derivatives of these compounds.

Of particular interest are the products of general formula (I) in which R' denotes a hydrogen atom, Z denotes an oxygen atom, p is equal to zero and A. either the symbol A denotes a heterocyclic ring such that, with the pyrrole nucleus with which it is condensed, it forms a 1H,3H-pyrrolo[1,2-c]thiazole, 2,3-dihydro1H-pyrrolizine,5,6,7,8-tetrahydroindolizine, 1,2-dihydro-4H-pyrrolo[1,2-c]-1,3-thiazine ring system, n is equal to zero, Het denotes a 3-pyridyl radical and (1) either R denotes a hydrogen atom and Y denotes an alkyl (preferably methyl) or phenyl radical, or Y denotes a radical of general formula (II) in which:

either $R_1$ denotes a hydrogen atom and $R_2$ denotes an unsubstituted alkyl radical, a cycloalkyl radical containing 3 to 6 carbon atoms, an alkenyl radical containing 2 to 4 carbon atoms, benzyl or phenyl radicals optionally substituted by a halogen atom or an alkyloxy or trifluoromethyl radical, or $R_2$ denotes an adamantyl, pyridyl or pyridylmethyl radical, or $R_1$ and $R_2$ both denote an unsubstituted alkyl radical or $R_1$ and $R_2$ form, with the nitrogen atom to which they are connected, a 4-phenylpiperazin-1-yl radical (2) or R denotes a halogen atom or an alkyl radical, and Y denotes an amino radical, B. or the symbol A denotes a heterocyclic ring such that, with the pyrrole nucleus with which it is condensed it forms a 2,3-dihydro-1H-pyrrolizine ring system substituted by a hydroxy radical, or a 2,3-dihydropyrrolo[2,1-b]thiazole ring system, R denotes a hydrogen radical, Y denotes an amino radical, n is equal to zero and Het denotes a 3-pyrridyl radical, C. or the symbol A denotes a heterocyclic ring such that, with the pyrrole nucleus with which it is condensed, it forms a 1H,3H-pyrrolo[1,2-c]thiazole ring system, R denotes a hydrogen atom, Y denotes an amino radical and either Het denotes a 5-thiazolyl radical and n is equal to zero or Het denotes a 3-pyridyl radical and n is equal to 1.

Of particular interest are the products of general formula (I) in which R' denotes a hydrogen atom, Z denotes an oxygen atom, p is equal to zero and A. either the symbol A denotes a heterocyclic ring such that, with the pyrrole nucleus with which it is condensed, it forms a 1H,3H-pyrrolo[1,2-c]thiazole, or 1,2-dihydro-4H-pyrrolo[1,2-c]-1,3-thiazine ring system, n is equal to zero, Het denotes a 3-pyridyl radical and (1) either R denotes a hydrogen atom and Y denotes a phenyl radical, or Y denotes a radical of general formula (II) in which $R_1$ denotes a hydrogen atom and $R_2$ denotes an unsubstituted alkyl radical, benzyl or phenyl radicals optionally substituted by a halogen atom or an alkyloxy radical, or $R_2$ denotes an adamantyl or pyridyl radical, (2) or R denotes a halogen atom or an alkyl radical, and Y denotes an amino radical, B. or the symbol A denotes a heterocyclic ring such that, with the pyrrole nucleus with which it is condensed, it forms a 2,3-dihydropyrrolo[2,1-b]thiazole ring system, R denotes a hydrogen atom, Y denotes an amino radical, n is equal to zero and Het denotes a 3-pyridyl radical.

The following products are of very particular interest:

N-(1-adamantyl)-5-(3-pyridyl)-1H,3H-pyrrolo[1,2-c]thiazole-7-carboxamide

N-(3-chlorophenyl)-5-(3-pyridyl)-1H,3H-pyrrolo[1,2-c]thiazole-7-carboxamide 7-benzoyl-5-(3-pyridyl)-1H,3H-pyrrolo[1,2-c]thiazole N-isopropyl-5-(3-pyridyl)-1H,3H-pyrrolo[1,2-c]thiazole-7- carboxamide N-benzyl-5-(3-pyridyl)-1H,3H-pyrrolo[1,2-c]thiazole-7-carboxamide 6-bromo-5-(3-pyridyl)-1H,3H-pyrrolo[1,2-c]thiazole-7-carboxamide N-(3-pyridyl)-5-(3-pyridyl)-1H,3H-pyrrolo[1,2-c]thiazole7-carboxamide N-methyl-5-(3-pyridyl)-1,2-dihydro-4H-pyrrolo[1,2-c]-1,3- thiazine-8-carboxamide 7-methyl-6-(3-pyridyl)-1,2-dihydro-4H-pyrrolo[1,2-c]-1,3- thiazine-8-carboxamide N-phenyl-6-(3-pyridyl)-1,2-dihydro-4H-pyrrolo[1,2-c]-1,3- thiazine-8-carboxamide N-(3-methoxyphenyl)-5-(3-pyridyl)-1H,3H-pyrrolo[1,2-c]- thiazole-7-carboxamide 5-(3-pyridyl)-2,3-dihydropyrrolo[2,1-b]thiazole-7-carboxamide, and N-methyl-5-(3-pyridyl)-1H,3H-pyrrolo[1,2-c]thiazole-7- carboxamide.

The following examples, given without implying a limitation, show how the invention may be put into practice:

EXAMPLE 1

A suspension of 7-chloroformyl-5-(3-pyridyl)-1H,3H-pyrrolo[1,2-c]thiazole hydrochloride (14.6 g) in methylene chloride (200 cc) is saturated with a stream of anhydrous monomethylamine while the temperature of the reaction mixture is kept at about 25° C. for 2 hours and 10 minutes. The suspension obtained is stirred at a temperature of about 20° C. for 16 hours. The crystals are separated off by filtration, washed 3 times with methylene chloride (90 cc in total) and suspended in a 2N aqueous solution of sodium hydroxide (100 cc). The crystals are separated off by filtration, washed 5 times with distilled water (250 cc in total) and 3 times with acetone (150 cc in total) and dried under reduced pressure (20 mm Hg; 2.7 kPa) at a temperature of about 20° C. in the presence of potassium hydroxide pellets. A product (11.3 g) melting at 252° C. is thus obtained. This product is dissolved in dimethylformamide (135 cc) at a temperature of about 100° C. The solution obtained is treated with decolourising charcoal (0.5 g) and filtered hot. The filtrate is cooled to a temperature of about 4° C. for one hour. The crystals which have appeared are separated off by filtration, washed twice with dimethylformamide (20 cc in total), 3 times with acetone (150 cc in total), and dried under reduced pressure (20 mm Hg; 2.7 kPa) at a temperature of about 20° C. in the presence of potassium hydroxide pellets. N-methyl-5-(3-pyridyl)-1H,3H-pyrrolo[1,2-c]thiazole-7-carboxamide (9.4 g) is thus obtained in the form of cream crystals melting at 254° C.

7-Chloroformyl-5-(3-pyridyl)-1H,3H-pyrrolo[1,2-c]thiazole hydrochloride may be prepared as follows:

A suspension of 5-(3-pyridyl)-1H,3H-pyrrolo[1,2-c]thiazole-7-carboxylic acid (8.8 g) in a mixture of thionyl chloride (6.25 cc), dimethylformamide (0.05 cc) and 1,2dichloroethane (100 cc) is heated under reflux with stirring for 2 hours and 30 minutes. The reaction mixture is cooled to a temperature of about 20° C. and concentrated to dryness under reduced pressure (20 mm Hg; 2.7 kPa) at a temperature of about 60° C. The residue obtained is suspended in cyclohexane (150 cc) and the solvent is evaporated off under reduced pressure (20 mm Hg; 2.7 kPa) at a temperature of about 60° C. The same procedure is repeated twice. 7- Chloroformyl-5-(3-pyridyl)-pyrrolo[1,2-c]thiazole hydrochloride (10 g) is thus obtained in the form of cream crystals melting at 220° C.

5-(3-Pyridyl)-1H,3H-pyrrolo[1,2-c]thiazole-7carboxylic acid may be prepared as follows:

A mixture of 5-(3-pyridyl)-1H,3H-pyrrolo[1,2-c]thiazole-7-carbonitrile (18.7 g), potassium hydroxide pellets (16.3 g) and ethylene glycol (160 cc) is heated with stirring at a temperature of about 155° C. for 2 hours. After 16 hours' stirring at a temperature of about 20° C., the solvent is evaporated off under reduced pressure (2 mm Hg; 0.27 kPa) at a temperature of about 100° C. The residue is dissolved in distilled water (100 cc) and the solution obtained is adjusted to a pH of about 5 by adding a 2 N aqueous solution of hydrochloric acid. The crystals which have appeared are separated off by filtration, washed 3 times with distilled water (150 cc in total), then 3 times with acetone (150 cc in total) and dried under reduced pressure (20 mm Hg; 2.7 kPa) at a temperature of about 20° C. in the presence of potassium hydroxide pellets. A crude product (17.7 g), melting at 264° C., is thus obtained. This product is combined with the product prepared in the same way in a previous operation (1.3 g) and dissolved in a mixture of 1-butanol (650 cc) and dimethylformamide (150 cc), heated beforehand to a temperature of about 115° C. Decolourising charcoal (0.5 g) is added to the solution obtained and is filtered off hot. The filtrate is cooled at a temperature of about 4° C. for 16 hours. The crystals which have appeared are separated off by filtration, washed twice with dimethylformamide (50 cc in total), 3 times with ethanol (150 cc in total), 3 times with isopropyl ether (150 cc in total) and then 3 times with diethyl ether (150 cc in total), and are dried under reduced pressure (20 mm Hg; 2.7 kPa) at a temperature of about 20° C. in the presence of potassium hydroxide pellets. A product (16.1 g) melting at 266° C. is thus obtained. This product is suspended in distilled water (250 cc) and the suspension is stirred for 2 hours at a temperature of about 20° C. The crystals are separated off by filtration, washed 5 times with distilled water (150 cc in total), 3 times with ethanol (90 cc in total), 3 times with isopropyl ether (90 cc in total) and then 3 times with diethyl ether (90 cc in total) and are dried under reduced pressure (20 mm Hg; 2.7 kPa) at a temperature of about 100° C. in the presence of potassium hydroxide pellets. 5-(3-Pyridyl)-1H,3H-pyrrolo[1,2-c]thiazole-7-carboxylic acid (15.5 g) is thus obtained in the form of cream crystals melting at 266° C.

5-(3-Pyridyl)-1H,3H-pyrrolo[1,2-c]thiazole-7-carbonitrile may be prepared in the following manner:

A suspension of N-nicotinoylthiazolidine-4-carboxylic acid (403 g) in a mixture of 2-chloroacrylonitrile (1,350 cc) and acetic anhydride (1,750 cc) is heated at 90° C. for 2 hours and 40 minutes. During this period, transient formation of a clear homogeneous phase is seen after 30 minutes, followed by precipitation 10 minutes later. After cooling at a temperature of about 4° C. for 16 hours, the crystals which have appeared are separated off by filtration, washed twice with acetic anhydride (200 cc in total), 3 times with acetone (300 cc in total) and are dried under reduced pressure (20 mm Hg; 2.7 kPa) at a temperature of about 20° C. in the presence of potassium hydroxide pellets. The product thus obtained is suspended in a 2 N aqueous solution of sodium hydroxide (2,400 cc). After stirring at a temperature of about 20° C. for 1 hour and 30 minutes, the crystals which have appeared are separated off by filtration, washed 5 times with distilled water (1,250 cc in total), 3 times with ethanol (1,200 cc in total), and 3 times with diethyl ether (900 cc in total), and are dried under reduced pressure (20 mm Hg; 2.7 kPa) at a temperature of about 20° C. in the presence of potassium hydroxide pellets. 5-(3-Pyridyl)-1H,3H-pyrrolo[1,2-c]thiazole-7-carbonitrile (159.7 g) is thus obtained in the form of cream crystals melting at 170° C.

N-nicotinoylthiazolidine-4-carboxylic acid may be obtained as follows:

Nicotinoyl chloride hydrochloride (534 g) is added over 1 hour at a temperature of between 30° and 52° C. to a solution of thiazolidine-4-carboxylic acid (400 g) and triethylamine (613 g) in chloroform (4,500 cc). The solution obtained is heated at a temperature of about 64° C. for 4 hours. After stirring at a temperature of about 20° C. for 16 hours, the crystals which have appeared are separated off by filtration, washed 3 times with chloroform (1,500 cc in total), then 3 times with diethyl ether (1,500 cc in total) and are dried under reduced pressure (20 mm Hg; 2.7 kPa) at a temperature of about 20° C. in the presence of potassium hydroxide pellets. N-nicotinoylthiazolidine-4-carboxylic acid (403 g) is thus obtained in the form of white crystals melting at 190° C.

EXAMPLE 2

A suspension of 7-chloroformyl-5-(3-pyridyl)-1H,3H-pyrrolo[1,2-c]thiazole hydrochloride (17.5 g) in methylene chloride (360 cc) is saturated for 3 hours and 30 minutes with a stream of anhydrous ethylamine at a temperature of between 17° C. and 30° C. The solution obtained is stirred at a temperature of about 20° C. for 16 hours and then methylene chloride (300 cc) and distilled water (300 cc) are added to it. The organic phase is separated off, washed twice with distilled water (600 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (12.5 g) melting at 165° C. is thus obtained. This product is dissolved in boiling ethanol (100 cc). The solution obtained is treated with decolourising charcoal (0.5 g) and filtered hot. The filtrate is cooled to a temperature of about 4° C. for 1 hour. The crystals which have appeared are separated off by filtration, washed twice with ethanol (10 cc in total) cooled to a temperature of about 4° C. and 3 times with diethyl ether (75 cc in total) and are dried under reduced pressure (20 mm Hg; 2.7 kPa) at a temperature of about 20° C. in the presence of potassium hydroxide pellets. A product (8.3 g) melting at 176° C. is thus obtained. This product is dissolved in boiling acetonitrile (225 cc). The solution obtained is treated with decolourising charcoal (0.5 g) and filtered hot. The filtrate is cooled at a temperature of about 4° C. for 1 hour. The crystals which have appeared are separated off by filtration, washed 3 times with acetonitrile (30 cc in total) and 3 times with diethyl ether (75 cc in total), and are then dried under reduced pressure (20 mm Hg; 2.7 kPa) at a temperature of about 20° C. in the presence of potassium hydroxide pellets. N-Ethyl-5-(3-pyridyl)-1H,3H-pyrrolo[1,2- c]thiazole-7-carboxamide (7.4 g) is thus obtained in the form of light yellow crystals melting at 178° C.

7-Chloroformyl-5-(3-pyridyl)-1H,3H-pyrrolo[1,2-c]thiazole hydrochloride is prepared as in Example 1.

EXAMPLE 3

A solution of isopropylamine (8.5 g) in methylene chloride (60 cc) is added over 15 minutes at a temperature of between 21° C. and 34° C. to a suspension of 7-chloroformyl-5-(3-pyridyl)-1H,3H-pyrrolo[1,2-c]thiazole hydrochloride (14.5 g) in methylene chloride (240 cc). The solution obtained is stirred at a temperature of about 20° C. for 16 hours and then methylene chloride (300 cc) and distilled water (250 cc) are added to it. The organic phase is separated off, washed 3 times with distilled water (750 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (13.5 g) melting at 200° C. is thus obtained. This product is dissolved in boiling acetonitrile (300 cc). The solution obtained is treated with decolourising charcoal (0.5 g) and filtered hot. The filtrate is cooled at a temperature of about 4° C. for 2 hours. The crystals which have appeared are separated off by filtration, washed twice with acetonitrile (50 cc in total) cooled to a temperature of about 4° C., twice with diethyl ether (100 cc in total) and are dried under reduced pressure (20 mm Hg; 2.7 kPa) at a temperature of about 20° C. in the presence of potassium hydroxide pellets. N-isopropyl-5-(3-pyridyl)-1H,3H-pyrrolo[1,2-c]thiazole-7-carboxamide (8.2 g) is thus obtained in the form of cream crystals melting at 218° C.

7-Chloroformyl-5-(3-pyridyl)-1H,3H-pyrrolo[1,2-c]thiazole hydrochloride is prepared as in Example 1.

EXAMPLE 4

A solution of butylamine (8.8 g) in methylene chloride (50 cc) is added over 15 minutes at a temperature of between 22° C. and 32° C. to a suspension of 7-chloroformyl-5-(3-pyridyl)-1H,3H-pyrrolo[1,2-c]thiazole hydrochloride (12 g) in methylene chloride (200 cc). The solution obtained is stirred at a temperature of about 20° C. for 16 hours and then methylene chloride (250 cc) and distilled water (200 cc) are added to it. The organic phase is separated off, washed twice with distilled water (400 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (9 g) melting at 140° C. is thus obtained. This product is dissolved in boiling acetonitrile (80 cc). The solution obtained is treated with decolourising charcoal (0.5 g) and filtered hot. The filtrate is cooled at a temperature of about 4° C. for 2 hours. The crystals which have appeared are separated off by filtration, washed twice with acetonitrile (30 cc in total) cooled to a temperature of about 4° C., and 3 times with diethyl ether (75 cc in total) and are dried under reduced pressure (20 mm Hg; 2.7 kPa) at a temperature of about 20° C. in the presence of potassium hydroxide pellets. N-butyl-5-(3-pyridyl)-1H,3H-pyrrolo[1,2-c]thiazole-7-carboxamide (7 g) is thus obtained in the form of cream crystals melting at 144° C.

7-Chloroformyl-5-(3-pyridyl)-1H,3H-pyrrolo[1,2-c]thiazole hydrochloride is prepared as in Example 1.

EXAMPLE 5

A suspension of 7-chloroformyl-5-(3-pyridyl)1H,3H-pyrrolo[1,2-c]thiazole hydrochloride (12 g) in methylene chloride (200 cc) is saturated with a stream of anhydrous dimethylamine while the temperature of the reaction mixture is kept at about 25° C. for 16 hours. Methylene chloride (250 cc) and 2 N aqueous solution of sodium hydroxide (100 cc) are added to the solution obtained. The organic phase is separated off, washed twice with a 2 N aqueous solution of sodium hydroxide (200 cc in total) and 3 times with distilled water (600 cc in total), dried over anhydrous potassium carbonate, treated with decolourising charcoal (0.5 g), filtered and concentrated to dryness under reduced pressure (20 mm Hg; 2.7 kPa) at a temperature of about 50° C. A product (10.7 g) is thus obtained. This product is dissolved in boiling acetonitrile (450 cc). The solution obtained is treated with decolourising charcoal (0.5 g) and filtered hot. The filtrate is cooled at a temperature of about 20° C. for 1 hour. The crystals which have appeared are separated off by filtration, washed 3 times with acetonitrile (90 cc in total) and 3 times with isopropyl ether (150 cc in total) and are dried under reduced pressure (20 mm Hg; 2.7 kPa) at a temperature of about 20° C. in the presence of potassium hydroxide pellets. N,N-dimethyl-5-(3-pyridyl)-1H,3H-pyrrolo[1,2-c]thiazole-7-carboxamide (7.5 g) is thus obtained in the form of white crystals melting at 200° C.

7-Chloroformyl-5-(3-pyridyl)-1H,3H-pyrrolo[1,2-c]thiazole hydrochloride is prepared as in Example 1.

EXAMPLE 6

A solution of benzylamine (12.9 g) in methylene chloride (50 cc) is added over 15 minutes at a temperature of between 22° C. and 29° C. to a suspension of 7-chloroformyl-5-(3-pyridyl)-1H,3H-pyrrolo[1,2-c]thiazole hydrochloride (12 g) in methylene chloride (200 cc). The suspension obtained is stirred at a temperature of about 20° C. for 16 hours and then methylene chloride (250 cc) and distilled water (250 cc) are added to it. The organic phase is separated off, washed 3 times with distilled water (750 cc in total), dried over anhydrous magnesium sulphate, treated with decolourising charcoal (0.5 g) filtered and concentrated to dryness under reduced pressure (20 mm Hg; 2.7 kPa) at a temperature of about 50° C. A product (10.8 g) melting at 130° C. is thus obtained. This product is dissolved in boiling acetonitrile (140 cc). The solution obtained is treated with decolourising charcoal (0.5 g) and filtered hot. The filtrate is cooled at a temperature of about 4° C. for about 2 hours. The crystals which have appeared are separated off by filtration, washed twice with acetonitrile (30 cc in total) cooled to a temperature of about 4° C. and 3 times with diethyl ether (75 cc in total) and are dried under reduced pressure (20 mm Hg; 2.7 kPa) at a temperature of about 20° C. in the presence of potassium hydroxide pellets. N-benzyl-5-(3-pyridyl)-1H,3H-pyrrolo[1,2-c]thiazole-7-carboxamide (7 g) is thus obtained in the form of pale yellow crystals melting at 150° C.

7-Chloroformyl-5-(3-pyridyl)-1H,3H-pyrrolo[1,2-c]thiazole hydrochloride is prepared as in Example 1.

EXAMPLE 7

A solution of cyclopropylamine (8.2 g) in methylene chloride (60 cc) is added over 15 minutes at a temperature of between 21° C. and 33° C. to a suspension of 7-chloroformyl-5-(3-pyridyl)-1H,3H-pyrrolo[1,2-c]thiazole hydrochloride (14.5 g) in methylene chloride (240 cc). The solution obtained is stirred at a temperature of about 20° C. for 16 hours; a product precipitates out. Methylene chloride (300 cc) and distilled water (250 cc) are added to the suspension obtained. The organic phase is separated off, washed 3 times with distilled water (750 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (13.5 g) melting at 180° C. is thus obtained. This product is dissolved in boiling acetonitrile (375 cc). The solution obtained is treated with decolourising charcoal (0.5 g) and filtered hot. The filtrate is cooled to a temperature of about 4° C. for 16 hours. The crystals which have appeared are separated off by filtration, washed twice with acetonitrile (50 cc in total) cooled to a temperature of about 4° C. and 3 times with isopropyl ether (150 cc in total), and are dried under reduced pressure (20 mm Hg; 2.7 kPa) at a temperature of about 20° C. in the presence of potassium hydroxide pellets. N-cyclopropyl-5-(3-pyridyl)-1H,3H-pyrrolo[1,2-c]thiazole-7-carboxamide (7.9 g) is thus obtained in the form of cream crystals melting at 184° C.

7-Chloroformyl-5-(3-pyridyl)-1H,3H-pyrrolo[1,2-c]thiazole hydrochloride is prepared as in Example 1.

EXAMPLE 8

A solution of 1-aminoadamantane (6.2 g) and triethylamine (8.1 g) in methylene chloride (50 cc) is added over 20 minutes at a temperature of between 21° C. and 30° C. to a suspension of 7-chloroformyl-5-(3-pyridyl)-1H,3H-pyrrolo[1,2-c]thiazole hydrochloride (12 g) in methylene chloride (200 cc). The solution obtained is stirred at a temperature of about 20° C. for 16 hours and then methylene chloride (250 cc) and distilled water (250 cc) are added to it. The organic phase is separated off, washed 3 times with distilled water (750 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (11.9 g) is thus obtained. This product is dissolved in boiling isopropanol (350 cc). The solution obtained is treated with decolourising charcoal (0.5 g) and filtered hot. The filtrate is cooled at a temperature of 4° C. for 2 hours. The crystals which have appeared are separated off by filtration, washed 3 times with isopropanol (30 cc in total) cooled to a temperature of about 4° C., and 3 times with isopropyl ether (150 cc) and are dried under reduced pressure (20 mm Hg; 2.7 kPa) at a temperature of about 20° C. in the presence of potassium hydroxide pellets. N-(1-adamantyl)-5-(3-pyridyl)-1H,3H-pyrrolo[1,2-c]thiazole-7-carboxamide (4.1 g) is thus obtained in the form of beige crystals melting at 214° C.

7-Chloroformyl-5-(3-pyridyl)-1H,3H-pyrrolo[1,2-c]thiazole hydrochloride is prepared as in Example 1.

EXAMPLE 9

A solution of allylamine (8.2 g) in methylene chloride (60 cc) is added over 15 minutes at a temperature of between 19° C. and 32° C. to a suspension of 7-chloroformyl-5-(3-pyridyl)-1H,3H-pyrrolo[1,2-c]thiazole hydrochloride (14.5 g) in methylene chloride (240 cc). The solution obtained is stirred at a temperature of about 20° C. for 16 hours and then methylene chloride (300 cc) and distilled water (300 cc) are added to it. The organic phase is separated, washed 3 times with distilled water (900 cc in total) dried over anhydrous magnesium sulphate, treated with decolourising charcoal (0.5 g), filtered and concentrated to dryness under reduced pressure (20 mm Hg; 2.7 kPa) at a temperature of about 50° C. A product (11 g) melting at 130° C. is thus obtained. This product is dissolved in boiling acetonitrile (140 cc). The solution obtained is treated with decolourising charcoal (0.5 g) and filtered hot. The filtrate is cooled at a temperature of about 20° C. for 2 hours. The crystals which have appeared are separated off by filtration, washed twice with acetonitrile (50 cc in total) and 3 times with isopropyl ether (150 cc in total) and dried under reduced pressure (20 mm Hg; 2.7 kPa) at a temperature of about 20° C. in the presence of potassium hydroxide pellets. N-allyl-5-(3-pyridyl)-1H,3H-pyrrolo[1,2-c]thiazole-7-carboxamide (6.7 g) is thus obtained in the form of beige crystals melting at 132° C.

7-Chloroformyl-5-(3-pyridyl)-1H,3H-pyrrolo[1,2-c]thiazole hydrochloride is prepared as in Example 1.

EXAMPLE 10

A solution of N-phenylpiperazine (28.2 g) in methylene chloride (150 cc) is added over 30 minutes at a temperature of between 26° C. and 33° C. to a suspension of 7-chloroformyl-5-(3-pyridyl)-1H,3H-pyrrolo[1,2-c]thiazole hydrochloride (15 g) in methylene chloride (300 cc). The suspension obtained is stirred at a temperature of about 20° C. for 16 hours and then methylene chloride (300 cc) and distilled water (250 cc) are added to it. The organic phase is separated off, washed twice with distilled water (500 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (22 g) is thus obtained. This product is dissolved in boiling acetonitrile (180 cc). The solution obtained is treated with decolourising charcoal (0.5 g) and filtered hot. The filtrate is cooled at a temperature of about 4° C. for 2 hours. The crystals which have appeared are separated by filtration, washed twice with acetonitrile (50 cc in total) and 3 times with diethyl ether (75 cc in total) and are dried under reduced pressure (20 mm Hg; 2.7 kPa)

at a temperature of about 20° C. in the presence of potassium hydroxide pellets. 7-[(4-Phenyl-1-piperazinyl)-carbonyl]-5-(3-pyridyl)-1H,3H-pyrrolo[1,2-c]thiazole (13.3 g) is thus obtained in the form of cream crystals melting at 160° C.

7-Chloroformyl-5-(3-pyridyl)-1H,3H-pyrrolo[1,2-c]thiazole hydrochloride is prepared as in Example 1.

EXAMPLE 11

Triethylamine (5.1 g) is added at a temperature of about 20° C. to a solution of the ethoxymagnesium derivative of diethyl malonate in a mixture (3:1 by volume) (65 cc) of diethyl ether and ethanol, prepared from magnesium (1.34 g) and diethyl malonate (8.8 g), and then 7-chloroformyl-5-(3-pyridyl)-1H,3H-pyrrolo[1,2-c]thiazole hydrochloride (15 g) is added over 5 minutes at a temperature of about 25° C. to the suspension obtained. During this period, the reaction mixture becomes clear and homogeneous before precipitation. The suspension obtained is stirred at a temperature of about 20° C. for 16 hours and then cooled at a temperature of about 4° C. and a 2 N aqueous solution of hydrochloric acid (30 cc) is added to it. After the mixtue has passed through a clear stage, precipitation is observed. The crystals which have appeared are separated off by filtration, washed 3 times with distilled water (90 cc in total) and are dried under reduced pressure (20 mm Hg; 2.7 kPa) at a temperature of about 20° C. A product (13.5 g) is thus obtained. The filtrate and the wash liquors are combined and extracted 3 times with ethyl acetate (240 cc in total). The organic extracts are combined, dried over anhydrous magnesium sulphate, treated with decolourising charcoal (0.5 g) filtered and concentrated to dryness under reduced pressure (20 mm Hg; 2.7 kPa) at a temperature of about 50° C. A product (6.1 g) is thus obtained. This product is combined with the product obtained earlier (13.5 g) and is dissolved in a mixture of acetic acid (25 cc), distilled water (15 cc) and concentrated sulphuric acid (3 cc). The solution obtained is heated at boiling point for 3 hours, then cooled to a temperature of about 20° C., diluted with distilled water (120 cc), treated with decolourising charcoal (0.5 g) and filtered. The filtrate is adjusted to a pH of about 10 by addition of 10 N aqueous solution of sodium hydroxide (17 cc). The crystals which have appeared are separated off by filtration, washed 3 times with 10 N sodium hydroxide (90 cc in total) and dried under reduced pressure (20 mm Hg; 2.7 kPa) at a temperature of about 20° C. in the presence of potassium hydroxide pellets. A product (9.4 g) melting at 155° C. is thus obtained. This product is dissolved in boiling ethanol (130 cc). The solution obtained is treated with decolourising charcoal (0.5 g) and filtered hot. The filtrate is cooled at a temperature of about 4° C. for 48 hours. The crystals which have appeared are separated off by filtration, washed twice with ethanol (20 cc in total) and 3 times with diethyl ether (30 cc in total) and are dried under reduced pressure (20 mm Hg; 2.7 kPa) at a temperature of about 20° C. in the presence of potassium hydroxide pellets. 7-Acetyl-5-(3-pyridyl)-1H,3H-pyrrolo[1,2-c]thiazole (7.2 g) is thus obtained in the form of pink beige crystals melting at 159° C.

7-Chloroformyl-5-(3-pyridyl)-1H,3H-pyrrolo[1,2-c]thiazole hydrochloride is prepared as in Example 1.

The ethoxymagnesium derivative of diethyl malonate is prepared according to G.A. REYNOLDS and C.R. HAUSER, Org. Synth., Coll. Vol. 4, 708 (1963).

EXAMPLE 12

A solution of 5-(3-pyridyl)-1H,3H-pyrrolo[1,2-c]thiazole-7-carbonitrile (22.7 g) in anhydrous tetrahydrofuran (300 cc) is added over 5 minutes at a temperature of about 40° C. to a solution of phenylmagnesium bromide in anhydrous tetrahydrofuran (390 cc) (prepared from bromobenzene (56.5 g) and magnesium (8.8 g)) and the suspension obtained is heated at a temperature of about 66° C. for 3 hours, after which distilled water (495 cc) followed by a 12 N aqueous solution of sulphuric acid (100 cc) are added to it at a temperature of about 10° C. The suspension obtained is stirred at a temperature of about 20° C. for 16 hours and then heated at boiling temperature for 7 hours and 30 minutes. The solution obtained is cooled to a temperature of about 20° C. and the suspension obtained is adjusted to a pH of about 10 at a temperature of about 20° C. by adding a 5 N aqueous solution of sodium hydroxide (250 cc). After 1 hour's stirring at a temperature of about 20° C., the suspension is filtered and the organic phase is separated off. The aqueous phase is extracted 3 times with ethyl acetate (750 cc in total) and the organic extracts are combined, washed 4 times with distilled water (1,000 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (25.2 g) melting at 135° C. is thus obtained. This product is chromatographed on a 4 cm diameter column containing silica (0.063–0.2 mm; 250 g), by eluting with mixtures of cyclohexane and ethyl acetate and collecting 250-cc fractions. The first two fractions from elution with a mixture of cyclohexane and ethyl acetate (50:50 by volume) are rejected. The next three fractions from elution with a mixture of cyclohexane and ethyl acetate (50:50 by volume) and the following three fractions from elution with pure ethyl acetate are combined and concentrated to dryness under reduced pressure (20 mm Hg; 2.7 kPa) at a temperature of about 50° C. A product (17.4 g) is thus obtained. This product is dissolved in boiling acetonitrile (150 cc). The solution obtained is treated with decolourising charcoal (0.5 g) and filtered hot. The filtrate is cooled at a temperature of about 4° C. for 1 hour. The crystals which have appeared are separated off by filtration, washed twice with acetonitrile (50 cc in total) cooled to a temperature of about 4° C. and 3 times with diethyl ether (75 cc in total) and are dried under reduced pressure (20 mm Hg; 2.7 kPa) at a temperature of about 20° C. in the presence of potassium hydroxide pellets. 7-Benzoyl-5-(3-pyridyl)-1H,3H-pyrrolo[1,2-c]thiazole (11.2 g) is thus obtained in the form of yellow crystals melting at 152° C.

5-(3-pyridyl)-1H,3H-pyrrolo[1,2-c]thiazole carbonitrile is prepared as in Example 1.

EXAMPLE 13

A solution of aniline (11.2 g) in methylene chloride (50 cc) is added over 15 minutes at a temperature of about 24° C. and 29° C. to a suspension of 7-chloroformyl-5-(3-pyridyl)-1H,3H-pyrrolo[1,2-c]thiazole hydrochloride (12 g) in methylene chloride (200 cc). The suspension obtained is stirred at a temperature of about 20° C. for 16 hours. Methylene chloride (300 cc) and distilled water (200 cc) are then added to the suspension. The insoluble material is separated off by filtration, washed 3 times with methylene chloride (75 cc in total) and 3 times with distilled water (75 cc in total). The mother-liquors from filtration and washing are combined; the organic phase is separated off, washed twice with distilled water (400 cc in total), once with a 2 N aqueous solution of sodium hydroxide (200 cc), then twice with distilled water (400 cc in total), dried over anhydrous magnesium sulphate, treated with decolourising charcoal (0.5 g) and filtered. A crude solution (625 cc) of product in methylene chloride is thus obtained. The insoluble material obtained earlier is taken up with a 5 N aqueous solution of sodium hydroxide (200 cc). The oil obtained is extracted 3 times with methylene chloride (750 cc in total). The organic extracts are combined, washed 3 times with distilled water (450 cc in total), dried over anhydrous magnesium sulphate, treated with decolourising charcoal (0.5 g) and filtered. The methylene chloride solution obtained is combined with the methylene chloride solution obtained earlier (625 cc) and the solvent is evaporated off under reduced pressure (20 mm Hg; 2.7 kPa) at a temperature of about 60° C. A crude product (15.4 g) is thus obtained. This product is dissolved in boiling acetonitrile (210 cc). The solution obtained is treated with decolourising charcoal (0.5 g) and filtered hot. The filtrate is cooled at a temperature of about 4° C. for 2 hours. The crystals which have appeared are separated off by filtration, washed 3 times with acetonitrile (30 cc in total) cooled to a temperature of about 4° C. and 3 times with isopropyl ether (75 cc in total) and are then dried under reduced pressure (20 mm Hg; 2.7 kPa) at a temperature of about 20° C. in the presence of potassium hydroxide pellets. N-phenyl-5-(3-pyridyl)-1H,3H-pyrrolo[1,2-c]thiazole-7-carboxamide (7.4 g) is thus obtained in the form of cream crystals melting at 188° C.

7-Chloroformyl-5-(3-pyridyl)-1H,3H-pyrrolo[1,2-c]thiazole hydrochloride is prepared as in Example 1.

EXAMPLE 14

A solution of bromine (17.1 g) in acetic acid (70 cc) is added over 20 minutes at a temperature of about 20° C. to a solution of 5-(3-pyridyl)-1H,3H-pyrrolo[1,2-c]thiazole-7-carboxamide (24.5 g) in acetic acid (330 cc). The suspension obtained is stirred at a temperature of about 20° C. for 3 hours. The crystals are then separated off by filtration, washed 3 times with acetic acid (150 cc in total), 3 times with acetone (150 cc in total) and 3 times with diethyl ether (150 cc in total) and then are dried under reduced pressure (20 mm Hg; 2.7 kPa) at a temperature of about 20° C. in the presence of potassium hydroxide pellets. The product obtained (60 g) is suspended in a 6.15 N aqueous solution of sodium hydroxide (1,300 cc). The crystals obtained are separated off by filtration, washed 4 times with distilled water (1,000 cc in total) and are dried under reduced pressure (20 mm Hg; 2.7 kPa) at a temperature of about 20° C. The product (28.5 g) thus obtained is chromatographed on a 4.2 cm diameter column containing silica (0.063–0.2 mm; 300 g) by eluting with mixtures of ethyl acetate and methanol and collecting 1,000-cc fractions. The first 3 fractions from the elution with pure ethyl acetate are combined and concentrated to dryness under reduced pressure (20 mm Hg; 2.7 kPa) at a temperature of about 60° C. A product (0.9 g) is thus obtained. The next 7 fractions from the elution with a mixture of ethyl acetate and methanol (95:5 by volume) and the following 3 fractions from the elution with a mixture of ethyl acetate and methanol (90:10 by volume) are combined and concentrated to dryness under reduced pressure (20 mm Hg; 2.7 kPa) at a temperature of about 60° C. A product (18.1 g) is thus obtained, which is suspended in a mixture (400 cc) of methylene chloride and methanol (96:4 by volume). The suspension obtained is filtered off and the filtrate is concentrated to dryness under reduced pressure (20 mm Hg; 2.7 kPa) at a temperature of about 60° C. A product (10.1 g) is thus obtained. This product is chromatographed on a 6 cm diameter column containing silica (0.04–0.063 mm; 480 g). Elution is carried out with a mixture of methylene chloride and methanol (96:4 by volume) under a pressure of 0.5 bar (51 kPa), 100-cc fractions being collected. The first 4 fractions are rejected, the following 13 fractions are combined and concentrated to dryness under reduced pressure (20 mm Hg; 2.7 kPa) at a temperature of about 60° C. A product (6.4 g) melting at 230° C. is thus obtained. This product, combined with the product obtained earlier (0.9 g) is dissolved in boiling 1-butanol (200 cc). The solution obtained is treated with decolourising charcoal (0.5 g) and filtered hot. The filtrate is cooled at a temperature of about 4° C. for 1 hour. The crystals which have appeared are separated off by filtration, washed twice with 1-butanol (50 cc in total), twice with ethanol (50 cc in total) and twice with diethyl ether (50 cc in total) and then are dried under reduced pressure (20 mm Hg; 2.7 kPa) at a temperature of about 20° C. in the presence of potassium hydroxide pellets. 6-Bromo-5-(3-pyridyl)-1H,3H-pyrrolo[1,2-c]thiazole-7-carboxamide (5.6 g) is thus obtained in the form of pale yellow crystals melting at 232° C.

5-(3-Pyridyl)-1H,3H-pyrrolo[1,2-c]thiazole-7-carboxamide may be prepared as follows:

A suspension of 5-(3-pyridyl)-1H,3H-pyrrolo[1,2-c]thiazole-7-carbonitrile (11.35 g) and of potassium hydroxide powder (14 g) in tert-butyl alcohol (100 cc) is heated at 85° C. for 1 hour. After 16 hours' stirring at a temperature of about 20° C., the reaction mixture is poured into distilled water (2 liters). The suspension is stirred at a temperature of about 20° C. for 15 minutes and then the crystals which have appeared are separated off by filtration, washed 8 times with distilled water (1,200 cc in total) and then 3 times with ethanol (150 cc in total) and are dried under reduced pressure (20 mm Hg; 2.7 kPa) at a temperature of about 20° C. in the presence of potassium hydroxide pellets. A crude product (10.5 g) is thus obtained which is combined with a product (3.9 g) prepared in the same manner in an earlier operation and dissolved in boiling ethanol (850 cc). The solution is treated with decolourising charcoal (0.5 g) and filtered hot. The filtrate is cooled at a temperature of about 4° C. for 3 days. The crystals which have appeared are separated off by filtration, washed 3 times with ethanol (30 cc in total) cooled to a temperature of about 4° C. and are dried under reduced pressure (20 mm Hg; 2.7 kPa) at a temperature of about 20° C. in the presence of potassium hydroxide pellets. 5-(3-Pyridyl)-1H,3H-pyrrolo[1,2-c]thiazole-7-carboxamide (11.3 g) is thus obtained in the form of cream crystals melting at 215° C.

EXAMPLE 15

A suspension of potassium hydroxide powder (3.6 g) and 6-methyl-5-(3-pyridyl)-1H,3H-pyrrolo[1,2-c]thiazole-7-carbonitrile (2.6 g) in tert-butyl alcohol (75 cc) is heated at a temperature of about 81° C. for 10 hours. The suspension is poured into distilled water (500 cc) and the solution obtained is stirred at a temperature of about 4° C. for 3 hours. The crystals which have appeared are separated off by filtration, washed 5 times with distilled water (125 cc in total) and are dried under reduced pressure (20 mm Hg; 2.7 kPa) at a temperature of about 20° C. in the presence of potassium hydroxide pellets. A product (2.3 g) melting at 212° C. is thus obtained. This product is dissolved in boiling ethanol (150 cc). The solution obtained is treated with decolourising charcoal (0.5 g) and filtered hot. The filtrate is cooled at a temperature of about 4° C. for 1 hour. The crystals which have appeared are separated off by filtration, washed twice with ethanol (50 cc in total) and 3 times with diethyl ether.(75 cc in total) and are dried under reduced pressure (20 mm Hg; 2.7 kPa) at a temperature of about 20° C. in the presence of potassium hydroxide pellets. 6-Methyl-5-(3-pyridyl)-1H,3H-pyrrolo[1,2-c]thiazole-7-carboxamide (1.6 g) is thus obtained in the form of white crystals melting at 222° C.

6-Methyl-5-(3-pyridyl)-1H,3H-pyrrolo[1,2-c]thiazole-7-carbonitrile may be prepared as follows:

A suspension of N-nicotinoylthiazolidine-4-carboxylic acid (19 g) and of 2-bromo-2-butenenitrile (58.4 g) in acetic anhydride (120 cc) is heated at a temperature of about 100° C. for 1 hour. The solution obtained is concentrated to dryness under reduced pressure (20 mm Hg; 2.7 kPa) at a temperature of about 50oC. The residue is suspended in distilled water (150 cc). A 10 N aqueous solution of sodium hydroxide (150 cc) is added to the suspension which is stirred at a temperature of about 20° C. for 30 minutes. Methylene chloride (300 cc) is then added; the organic phase is separated off and the aqueous phase is extracted twice with methylene chloride (600 cc in total). The organic extracts are combined, washed 3 times with distilled water (300 cc in total), dried over anhydrous magnesium sulphate, treated with decolourising charcoal (0.5 g), filtered and concentrated to dryness under reduced pressure (20 mm Hg; 2.7 kPa) at a temperature of about 60° C. A crude product (2.6 g) is thus obtained. This product is chromatographed on a 4 cm diameter column containing silica (0.04–0.063 mm; 320 g). It is eluted with a mixture of ethyl acetate and cyclohexane (70:30 by volume) under a pressure of 0.5 bar (51 kPa), 50 cc fractions being collected. The first 9 fractions are rejected; the following 8 fractions are combined and concentrated to dryness under reduced pressure (20 mm Hg; 2.7 kPa) at a temperature of about 60° C. A product (1.1 g) is thus obtained. This product is combined with a product (4 g) prepared in the same way in previous operations and is dissolved in boiling acetonitrile (75 cc). The solution obtained is filtered hot. The filtrate is cooled to a temperature of about 20° C. The crystals which have appeared are separated off by filtration, washed twice with acetonitrile (20 cc in total) and 3 times with diethyl ether (75 cc in total) and are dried under reduced pressure (20 mm Hg; 2.7 kPa) at a temperature of about 20° C. in the presence of potassium hydroxide pellets. 6-Methyl-5-(3-pyridyl)-1H,3H-pyrrolo[1,2-c]thiazole-7-carbonitrile (2.6 g) is thus obtained in the form of cream crystals melting at 190° C.

N-Nicotinoylthiazolidine-4-carboxylic acid is prepared as in Example 1.

2-Bromo-2-butenenitrile may be prepared according to L. LECLERCQ and A. BRUYLANTS, Bull. Soc. chim. belges, 58, 5 (1949).

EXAMPLE 16

A solution of 3-chloroaniline (6.4 g) and of triethylamine (10.1 g) in methylene chloride (100 cc) is added over 30 minutes at a temperature of between 26° and 34° C. to a suspension of 7-chloroformyl-5-(3-pyridyl)-1H,3H-pyrrolo[1,2-c]thiazole hydrochloride (15 g) in methylene chloride (250 cc). The solution obtained is stirred at a temperature of about 20° C. for 16 hours. A product precipitates out. The crystals which have appeared are separated off by filtration, washed 4 times with methylene chloride (400 cc in total) and are dried under reduced pressure (20 mm Hg; 2.7 kPa) at a temperature of about 20° C. in the presence of potassium hydroxide pellets. A product (9 g) melting at 200° C. is thus obtained. The earlier filtrates are combined, washed 4 times with distilled water (800 cc in total) and are dried over anhydrous magnesium sulphate and concentrated to dryness under reduced pressure (20 mm Hg; 2.7 kPa) at a temperature of about 60° C. A product (7 g) melting at 198° C. is thus obtained which is combined with product obtained earlier (9 g) and is dissolved in boiling 1-butanol (250 cc). The solution obtained is treated with decolourising charcoal (0.5 g) and filtered hot; the filtrate is cooled at a temperature of about 4° C. for 16 hours. The crystals which have appeared are separated off by filtration, washed 3 times with 1-butanol (75 cc in total), 3 times with ethanol (75 cc in total) and 3 times with diethyl ether (150 cc in total) and are then dried under reduced pressure (20 mm Hg; 2.7 kPa) at a temperature of about 20° C. in the presence of potassium hydroxide pellets.

N-(3-Chlorophenyl)-5-(3-pyridyl)-1H,3H-pyrrolo[1,2-c]thiazole-7-carboxamide (11.9 g) is thus obtained in the form of cream crystals melting at 206° C.

7-Chloroformyl-5-(3-pyridyl)-1H,3H-pyrrolo[1,2-c]thiazole hydrochloride is prepared as in Example 1.

EXAMPLE 17

A suspension of 7-chloroformyl-5-(3-pyridyl)-2,3-dihydro-1H-pyrrolizine hydrochloride (14.1 g) in methylene chloride (250 cc) is saturated with a stream of anhydrous methylamine, while the temperature of the reaction mixture is kept at about 25° C. for 7 hours. The solution obtained is stirred at a temperature of about 20° C. for 16 hours and then methylene chloride (250 cc) and distilled water (250 cc) are added to it. The organic phase is separated, washed 3 times with distilled water (750 cc in total), dried over anhydrous magnesium sulphate, treated with decolourising charcoal (0.5 g), filtered and concentrated to dryness under reduced pressure (20 mm Hg; 2.7 kPa) at a temperature of about 60° C. A crude product (12.2 g) melting at 184° 0 is thus obtained. This product is dissolved in boiling acetonitrile (150 cc). The solution obtained is treated with decolourising charcoal (0.5 g) and filtered hot. The filtrate is cooled at a temperature of about 4° C. for 1 hour. The crystals which have appeared are separated off by filtration, washed twice with acetonitrile (20 cc in total) cooled to a temperature of about 4° C. and 3 times with diethyl ether (75 cc in total), and then dried under reduced pressure (20 mm Hg; 2.7 kPa) at a temperature of about 20° C. in the presence of potassium hydroxide pellets. N-methyl-5-(3-pyridyl)-2,3-dihydro-1H-pyrrolizine-7-carboxamide (7.1 g) is thus obtained in the form of cream crystals melting at 187° C.

7-Chloroformyl-5-(3-pyridyl)-2,3-dihydro-1H-pyrrolizine hydrochloride may be prepared as follows:

A suspension of 5-(3-pyridyl)-2,3-dihydro-1H-pyrrolizine-7-carboxylic acid (11.4 g) in a mixture of thionyl chloride (17.4 cc), dimethylformamide (0.05 cc) and 1,2-dichloroethane (150 cc) is heated at a temperature of about 80° C. for 3 hours. The reaction mixture is cooled to a temperature of about 20° C. and concentrated to dryness under reduced pressure (20 mm Hg; 2.7 kPa) at a temperature of about 60° C. The residue obtained is suspended in cyclohexane (250 cc) and the solvent is evaporated off under reduced pressure (20 mm Hg; 2.7 kPa) at a temperature of about 60° C. The same operation is repeated twice. 7-Chloroformyl-5-(3-pyridyl)-2,3-dihydro-1H-pyrrolizine hydrochloride (14.1 g) is thus obtained in the form of yellow crystals melting at 230° C.

5-(3-Pyridyl)-2,3-dihydro-1H-pyrrolizine-7-carboxylic acid may be prepared as follows:

A suspension of 5-(3-pyridyl)-2,3-dihydro-1H-pyrrolizine-7-carbonitrile (41.9 g) and of potassium hydroxide powder (39.6 g) in ethylene glycol (400 cc) is heated to a temperature of about 160° C. The solution obtained is kept at a temperature of about 160° C. for 3 hours. The solvent is evaporated off under reduced pressure (20 mm Hg; 2.7 kPa) at a temperature of about 110° C. The residue obtained is dissolved in distilled water (1,100 cc) and the solution is adjusted to a pH of about 5 by addition of a 2 N aqueous solution of hydrochloric acid (300 cc). The suspension obtained is stirred at a temperature of about 20° C. for 1 hour. The crystals are separated off by filtration, washed twice with distilled water (500 cc in total) and dried in air and then under reduced pressure (20 mm Hg; 2.7 kPa) at a temperature of about 20° C. in the presence of potassium hydroxide pellets. A crude hydrated product (58 g) melting at 220° C. is thus obtained. The product is taken up with boiling ethanol (1,500 cc) and the suspension obtained is filtered hot. The filtrate is cooled at a temperature of about 4° C. for 16 hours. The crystals which have appeared are separated off by filtration, washed 3 times with ethanol (300 cc in total) and 3 times with diethyl ether (300 cc in total) and are then dried under reduced pressure (20 mm Hg; 2.7 kPa) at a temperature of about 20° C. in the presence of potassium hydroxide pellets. 5-(3-Pyridyl)-2,3-dihydro-1H-pyrrolizine-7-carboxylic acid (29.4 g) is thus obtained in the form of pale yellow crystals melting at 240° C.

5-(3-Pyridyl)-2,3-dihydro-1H-pyrrolizinecarbonitrile may be prepared as described in the European Patent Application published under No. 0,118,321.

EXAMPLE 18

A suspension of 1-chloroformyl-3-(3-pyridyl)-5,6,7,8-tetrahydroindolizine hydrochloride (16.3 g) in methylene chloride (275 cc) is saturated with a stream of anhydrous methylamine while the temperature of the reaction mixture is kept at about 25° C. for 7 hours. The solution obtained is stirred at a temperature of about 20° C. for 16 hours and then methylene chloride (500 cc) and distilled water (300 cc) are added to it. The organic phase is separated off, washed 4 times with distilled water (1,200 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A product (13.9 g) melting at 168° C. is thus obtained. This product is dissolved in boiling acetonitrile (150 cc). The solution obtained is treated with decolourising charcoal (0.5 g) and filtered hot. The filtrate is cooled at a temperature of about 4° C. for 1 hour. The crystals which have appeared are separated off by filtration, washed 3 times with acetonitrile (30 cc in total) cooled to a temperature of about 4° C. and 3 times with diethyl ether (75 cc in total) and are then dried under reduced pressure (20 mm Hg; 2.7 kPa) at a temperature of about 20° C. in the presence of potassium hydroxide pellets. N-methyl-3-(3-pyridyl)-5,6,7,8-tetrahydroindolizine-1-carboxamide (8.3 g) is thus obtained in the form of light yellow crystals melting at 170° C.

1-Chloroformyl-3-(3-pyridyl)-5,6,7,8-tetrahydroindolizine hydrochloride may be prepared as follows:

A solution of 3-(3-pyridyl)-5,6,7,8-tetrahydroindolizine-1-carboxylic acid (13.3 g) in a mixture of thionyl chloride (19.2 cc), dimethylformamide (0.05 cc) and 1,2-dichloroethane (160 cc) is heated to a temperature of about 70° C. The suspension obtained is kept at a temperature of about 70° C. for 3 hours. The reaction mixture is cooled to a temperature of about 20° C. and concentrated to dryness under reduced pressure (20 mm Hg; 2.7 kPa) at a temperature of about 60° C. The residue is suspended in cyclohexane (300 cc) and the solvent is evaporated off under reduced pressure (20 mm Hg; 2.7 kPa) at a temperature of about 60° C. The same operation is repeated twice. 1-Chloroformyl-3-(3-pyridyl)-5,6,7,8-tetrahydroindolizine hydrochloride (16.3 g) is thus obtained in the form of light green crystals melting at 205° C.

3-(3-Pyridyl)-5,6,7,8-tetrahydroindolizine-1-carboxylic acid may be prepared as follows:

A solution of 3-(3-pyridyl)-5,6,7,8-tetrahydroindolizine-1-carbonitrile (15.6 g) and of potassium hydroxide powder (15.8 g) in ethylene glycol (150 cc) is heated at a temperature of about 156° C. for 11 hours and 30 minutes. After 16 hours' stirring at a temperature of about 20° C., the solvent is evaporated off under reduced pressure (2 mm Hg; 0.27 kPa) at a temperature of about 100° C. The residue obtained is dissolved in distilled water (250 cc). The solution obtained is treated with decolourising charcoal (0.5 g) and filtered. The filtrate is adjusted to a pH of about 5 at a temperature of about 25° C. by addition of a 5 N aqueous solution of hydrochloric acid (50 cc). The suspension obtained is stirred at a temperature of about 20° C. for 1 hour. The crystals are separated off by filtration, washed 5 times with distilled water (250 cc in total) and then dried in air. 3-(3-Pyridyl)-5,6,7,8-tetrahydroindolizine-1-carboxylic acid (13.4 g) is thus obtained in the form of beige crystals melting at 198° C.

3-(3-Pyridyl)-5,6,7,8-tetrahydroindolizine-1-carbonitrile is prepared as described in the European Patent Application published under No. 0,118,321.

EXAMPLE 19

A suspension of N-nicotinoyl-3,4,5,6-tetrahydro-2H-1,3-thiazine-4-carboxylic acid (27.3 g) in acetic anhydride (250 cc) is heated to a temperature of about 95° C. A solution of N-methylpropiolamide (18 g) in acetic anhydride (190 cc) is added over 15 minutes to the solution obtained, while the temperature is kept at about 95° C. This temperature is maintained for another hour. A suspension is then obtained. This suspension is cooled at a temperature of about 4° C. for 1 hour. The crystals which have appeared are separated off by filtration, washed twice with acetic anhydride (20 cc in total) cooled to a temperature of about 4° C. and 3 times with diethyl ether (60 cc in total) and then dried under reduced pressure (20 mm Hg; 2.7 kPa) at a temperature of about 20° C. in the presence of potassium hydroxide pellets. A product (12 g) melting at 245° C. is thus obtained. This product is dissolved in boiling 1-butanol (200 cc). The solution obtained is treated with decolourising charcoal (0.5 g) and filtered hot. The filtrate is cooled at a temperature of about 4° C. for 1 hour. The crystals which have appeared are separated off by filtration, washed twice with 1-butanol (20 cc in total) cooled to a temperature of about 4° C. and 4 times with diethyl ether (200 cc in total), and then dried under reduced pressure (20 mm Hg; 2.7 kPa) at a temperature of about 20° C. in the presence of potassium hydroxide pellets. N-methyl-6-(3-pyridyl)-1,2-dihydro-4H-pyrrolo[1,2-c]-1,3-thiazine-8-carboxamide (10.5 g) is thus obtained in the form of yellow crystals melting at 248° C.

N-nicotinoyl-3,4,5,6-tetrahydro-2H-1,3-thiazine-4-carboxylic acid is prepared as described in the European Patent Application published under No. 0,118,321.

N-methylpropiolamide is prepared according to W. D. CROW and N. J. LEONARD, J. Org. Chem., 30, 2660 (1965).

EXAMPLE 20

A solution of 3-aminopyridine (4.7 g) and of triethylamine (10.2 g) in methylene chloride (100 cc) is added over 15 minutes at a temperature of between 20° and 30° C. to a suspension of 7-chloroformyl-5-(3-pyridyl)pyrrolo[1,2-c]thiazole hydrochloride (15 g) in methylene chloride (250 cc). The solution obtained is stirred at a temperature of about 20° C. for 16 hours. A product precipitates out. The crystals are separated off by filtration, washed 4 times with methylene chloride (200 cc in total), 3 times with distilled water (200 cc in total), twice with a 2 N aqueous solution of sodium hydroxide (200 cc in total), 4 times with distilled water (200 cc in total), 3 times with acetone (75 cc in total) and 3 times with diethyl ether (75 cc in total) and then dried under reduced pressure (20 mm Hg; 2.7 kPa) at a temperature of about 20° C. in the presence of potassium hydroxide pellets. A product (13.2 g) melting at 260° C. is thus obtained. This product is dissolved in boiling dimethylformamide (110 cc). The solution obtained is treated with decolourising charcoal (0.5 g) and filtered hot. The filtrate is cooled at a temperature of about 4° C. for 2 hours. The crystals which have appeared are separated off by filtration, washed 3 times with dimethylformamide (30 cc in total) cooled to a temperature of about 4° C., 3 times with ethanol (75 cc in total) and 3 times with diethyl ether (75 cc in total) and then dried under reduced pressure (20 mm Hg; 2.7 kPa) at a temperature of about 20° C. in the presence of potassium hydroxide pellets. N-(3-pyridyl)-5-(3-pyridyl)-1H,3H-pyrrolo[1,2-c]thiazole-7-carboxamide (11.6 g) is thus obtained in the form of beige crystals melting at 278° C.

7-Chloroformyl-5-(3-pyridyl)-pyrrolo[1,2-c]thiazole hydrochloride is prepared as in Example 1.

EXAMPLE 21

A solution of 3-aminomethylpyridine (5.5 g) and of triethylamine (10.1 g) in methylene chloride (100 cc) is added over 15 minutes at a temperature between 20° and 30° C. to a suspension of 7-chloroformyl-5-(3-pyridyl)-1H,3H-pyrrolo[1,2-c]thiazole hydrochloride (15 g) in methylene chloride (250 cc). The solution obtained is stirred at a temperature of about 20° C. for 16 hours. A product precipitates out. The crystals which have appeared are separated off by filtration, washed 3 times with methylene chloride (300 cc in total) and 3 times with isopropyl ether (200 cc in total) and then dried under reduced pressure (20 mm Hg; 2.7 kPa) at a temperature of about 20° C. in the presence of potassium hydroxide pellets. A crude product (11.3 g) melting at 206° C. is thus obtained. This product is dissolved in boiling 1-butanol (160 cc). The solution obtained is treated with decolourising charcoal (0.5 g) and filtered hot. The filtrate is cooled at a temperature of about 4° C. for 2 hours. The crystals which have appeared are separated off by filtration, washed 4 times with 1-butanol (100 cc in total) and 4 times with diethyl ether (100 cc in total) and are then dried under reduced pressure (20 mm Hg; 2.7 kPa) at a temperature of about 20° C. in the presence of potassium hydroxide pellets. N-(3-pyridylmethyl)-5-(3-pyridyl)-1H,3H-pyrrolo[1,2-c]thiazole-7-carboxamide (9.9 g) is thus obtained in the form of cream crystals melting at 210° C.

7-Chloroformyl-5-(3-pyridyl)-1H,3H-pyrrolo[1,2-c]thiazole hydrochloride is prepared as in Example 1.

EXAMPLE 22

A suspension of 2-[5-(3-pyridyl)-1H,3H-pyrrolo[1,2-c]thiazol-7-yl]acetonitrile (6.5 g) and of potassium hydroxide powder (8.9 g) in tert-butyl alcohol (110 cc) is heated at a temperature of about 80° C. for 15 minutes. The suspension is poured into distilled water (1,500 cc) and the mixture is extracted 4 times with methylene chloride (1,200 cc in total). The organic extracts are combined, washed 3 times with distilled water (750 cc in total), dried over anhydrous magnesium sulphate, treated with decolourising charcoal (0.5 g), filtered and concentrated to dryness under reduced pressure (20 mm Hg; 2.7 kPa) at a temperature of about 60° C. A product (4.9 g) melting at 174° C. is thus obtained. This product is combined with an identical product (0.6 g) prepared in another, earlier operation and the whole is dissolved in boiling ethanol (150 cc). The solution obtained is treated with decolourising charcoal (0.5 g) and filtered hot. The filtrate is cooled at a temperature of about 4° C. for 1 hour. The crystals which have appeared are separated off by filtration, washed 3 times with ethanol (75 cc in total) cooled to a temperature of about 4° C. and 3 times with diethyl ether (75 cc in total) and then dried under reduced pressure (20 mm Hg; 2.7 kPa) at a temperature of about 20° C. in the presence of potassium hydroxide pellets. 2-[5-(3-pyridyl)-1H,3H-pyrrolo[1,2-c]thiazol-7-yl]acetamide (3.4 g) is thus obtained in the form of pale yellow crystals melting at 176° C.

2-[5-(3-Pyridyl)-1H,3H-pyrrolo[1,2-c]thiazol-7-yl]acetonitrile may be prepared as follows:

A solution of tosylmethyl isocyanide (7.5 g) in 1,2-dimethoxyethane (50 cc) is added over 20 minutes at a temperature of about −30° C. to a solution of potassium tert-butylate (8.7 g) in 1,2-dimethoxyethane (140 cc) cooled to a temperature of about −30° C. The solution obtained is cooled to a temperature of about −60° C., and then a solution of 5-(3-pyridyl)-1H,3H-pyrrolo[1,2-c]thiazole-7-carboxaldehyde (8 g) in 1,2-dimethoxyethane (70 cc) is added to it over 30 minutes at a temperature of about −60° C. The solution obtained is brought to a temperature of about 0° C. over 1 hour and then kept at this temperature for 1 hour and 20 minutes. Methanol (105 cc) is then added over 15 minutes, at a temperature of between 3 and 7° C. The solution obtained is heated at a temperature of about 72° C. for 1 hour and 15 minutes and is then stirred at a temperature of about 20° C. for 16 hours. Three-quarters of the solvent are evaporated off under reduced pressure (20 mm Hg; 2.7 kPa) at a temperature of about 40° C. The residue is taken up with a mixture of distilled water (350 cc) and ethyl acetate (250 cc). The organic phase is separated off and the aqueous phase is extracted 3 times with ethyl acetate (750 cc in total). The organic extracts are combined, washed 3 times with distilled water (450 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A crude product (7.6 g) is thus obtained. This product is chromatographed on a 2.7 cm diameter column containing silica (0.063–0.2 mm; 75 g) by eluting with mixtures of cyclohexane and ethyl acetate and collecting 200-cc fractions. The first 2 fractions from the elution with a mixture of cyclohexane and ethyl acetate (50:50 by volume) are rejected. The next 3 fractions from the elution with a mixture of cyclohexane and ethyl acetate (50:50 by volume) and the following fraction from the elution with pure ethyl acetate, are combined and concentrated to dryness under reduced pressure (20 mm Hg; 2.7 kPa) at a temperature of about 60° C. 2-[-5-(3-Pyridyl)-1H,3H-pyrrolo[1,2-c]thiazol-7-yl]acetonitrile (6 g) is thus obtained in the form of light yellow crystals melting at 92° C.

5-(3-Pyridyl)-1H,3H-pyrrolo[1,2-c]thiazole-7-carboxaldehyde is prepared as described in the European Patent Application published under No. 0,118,321.

EXAMPLE 23

A suspension of potassium hydroxide powder (6.5 g) and of a mixture (in 20:80 proportion) (4.6 g) of 6-cyano and of 7-cyano-5-(5-thiazolyl)-1H,3H-pyrrolo[1,2-c]thiazole in tert-butyl alcohol (100 cc) is heated to reflux temperature for 2 minutes in a bath preheated to 100° C. The resulting suspension is poured into distilled water (800 cc) and the crystals obtained are separated off by filtration, washed 6 times with distilled water (300 cc in total) and 3 times with acetone (75 cc in total) and then dried under reduced pressure (20 mm Hg; 2.7 kPa) at a temperature of about 20° C. in the presence of potassium hydroxide pellets. A product (1.8 g) melting at 230° C. is thus obtained. The above filtrate is extracted 3 times with methylene chloride (1,000 cc in total) and 3 times with ethyl acetate (1,000 cc in total). The organic extracts are combined, dried over anhydrous magnesium sulphate, filtered and concentrated to dryness under reduced pressure (20 mm Hg; 2.7 kPa) at a temperature of about 60° C. A product (1 g) melting at 215° C. is thus obtained. This product is combined with the 1.8 g obtained earlier and with an identical product (1.2 g) originating from another, earlier operation. The three lots are dissolved in boiling 1-butanol (200 cc). The solution obtained is treated with decolourising charcoal (0.5 g) and filtered hot. The filtrate is cooled at a temperature of about 4° C. for 2 hours. The crystals which have appeared are separated off by filtration, washed twice with 1-butanol (20 cc in total), twice with ethanol (50 cc in total) and 3 times with diethyl ether (75 cc in total) and then dried under reduced pressure (20 mm Hg; 2.7 kPa) at a temperature of about 20° C. in the presence of potassium hydroxide pellets. 5-(5-Thiazolyl)-1H,3H-pyrrolo[1,2-c]thiazole-7-carboxamide (2.1 g) is thus obtained in the form of orange crystals melting at 236° C.

The mixture (20:80) of 6-cyano and 7-cyano-5-(5-thiazolyl)-1H,3H-pyrrolo[1,2-c]thiazole may be prepared as follows:

A solution of 5-chloroformylthiazole (14.1 g) in chloroform (120 cc) is added over 15 minutes at a temperature of between 23° and 36° C. to a solution of thiazolidine-4-carboxylic acid (13.1 g) and of triethylamine (9.8 g) in chloroform (360 cc). The solution obtained is heated at a temperature of about 64° C. for 2 hours and 15 minutes. After stirring at a temperature of about 20° C. for 16 hours, the solvent is evaporated off under reduced pressure (20 mm Hg; 2.7 kPa) at a temperature of about 60° C. and the residue is taken up with acetone (350 cc). The suspension obtained is filtered and the filtrate is concentrated to dryness under reduced pressure (20 mm Hg; 2.7 kPa) at a temperature of about 60° C. A product (26.4 g) is thus obtained, and is dissolved in a mixture of 2-chloroacrylonitrile (77 cc) and acetic anhydride (96 cc). The solution obtained is heated at a temperature of about 90° C. for 2 hours and 45 minutes, and is then stirred at a temperature of about 20° C. for 16 hours. The crystals which have appeared are separated off by filtration, washed twice with acetic anhydride (150 cc in total) and 3 times with acetone (225 cc in total) and then dried under reduced pressure (20 mm Hg; 2.7 kPa) at a temperature of about 20° C. in the presence of potassium hydroxide pellets. A product (7.2 g) is thus obtained. This product is suspended in distilled water (150 cc). A 10N aqueous solution of sodium hydroxide (150 cc) is added to the suspension. The crystals which have appeared are separated off by filtration, washed 4 times with distilled water (200 cc in total) and are dried under reduced pressure (20 mm Hg; 2.7 kPa) at a temperature of about 20° C. in the presence of potassium hydroxide pellets. A mixture (4.6 g) of 6-cyano and 7-cyano-5-(5-thiazolyl)-1H,3H-pyrrolo[1,2-c]thiazole is thus obtained, in the form of reddish brown crystals melting at 155° C., in a ratio of 20:80 (according to the NMR spectrum).

EXAMPLE 24

A solution of 7-methyl-6-(3-pyridyl)-1,2-dihydro-4H-pyrrolo[1,2-c]-1,3-thiazine-8-carbonitrile (5.5 g) in a 12N aqueous solution of hydrochloric acid (70 cc) is heated with stirring at a temperature of between 80° and 86° C. for 1 hour and 30 minutes and then at a temperature of about 96° C. for 7 hours and 30 minutes. The solution obtained is stirred at a temperature of about 20° C. for 16 hours, then a 12N aqueous solution of hydrochloric acid (20 cc) is added to it and it is heated at a temperature of about 98° C. for 6 hours and 30 minutes. Distilled water (100 cc) is added to the solution obtained and the latter is adjusted to a pH of about 9 by addition of potassium carbonate. The suspension obtained is extracted 3 times with a mixture of methylene chloride and methanol (9:1 by volume; 450 cc in total). The organic extracts are combined, washed twice with distilled water (100 cc in total), dried over anhydrous magnesium sulphate, treated with decolourising charcoal (0.5 g), filtered and concentrated under reduced pressure (20 mm Hg; 2.7 kPa) at a temperature of about 50° C. A crude product (4.8 g) is thus obtained and is chromatographed on a 6 cm diameter column containing silica (0.04–0.063 mm; 480 g). It is eluted with a mixture of ethyl acetate and methanol (95:5 by volume) under a pressure of 0.5 bar (51 kPa) and 200-cc fractions are collected. The first 9 fractions are rejected; the next 5 fractions are combined and concentrated to dryness under reduced pressure (20 mm Hg; 2.7 kPa) at a temperature of about 50° C. A product (1.8 g) is thus obtained, and combined with a product (0.3 g) prepared in the same way in a previous operation, and is dissolved in boiling ethanol (60 cc): The solution obtained is treated with decolourising charcoal (0.5 g) and filtered hot. The filtrate is cooled at a temperature of about 4° C. for 16 hours. The crystals which have appeared are separated off by filtration, washed twice with ethanol (4 cc in total) cooled to a temperature of about 4° C., and 3 times with diethyl ether (12 cc in total), and then dried under reduced pressure (20 mm Hg; 2.7 kPa) at a temperature of about 20° C. in the presence of potassium hydroxide pellets. 7-Methyl-6-(3-pyridyl)-1,2-dihydro-4H-pyrrolo[1,2-c]-1,3-thiazine-8-carboxamide (1.3 g) is thus obtained in the form of white crystals melting at 220° C.

7-Methyl-6-(3-pyridyl)-1,2-dihydro-4H-pyrrolo[1,2-c]-1,3-thiazine-8-carbonitrile may be prepared as follows:

2-Chlorocrotononitrile (36 g) is added over 8 minutes, at a temperature of about 80° C., to a solution of N-nicotinoyl-3,4,5,6-tetrahydro-2H-1,3-thiazine-4-carboxylic acid (9 g) in acetic anhydride (100 cc). The solution obtained is heated at a temperature between 85° and 90° C. for 3 hours and then the solvent is evaporated off under reduced pressure (20 mm Hg; 2.7 kPa) at a temperature of about 80° C. The residual oil is dissolved in distilled water (100 cc) and the solution obtained is adjusted to a pH of about 10 by addition of solid potassium carbonate followed by a 4N aqueous solution of sodium hydroxide (10 cc). This basic solution is extracted 5 times with ethyl acetate (500 cc in total). The organic extracts are combined, washed 5 times with distilled water (400 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. A crude product (6.9 g) melting at 130° C. is thus obtained which, combined with the product (4.3 g) obtained in the same way in another operation, is dissolved in boiling isopropanol (60 cc). The solution obtained is treated with decolourising charcoal (0.5 g) and filtered hot. The filtrate is cooled at a temperature of about 4° C. for 16 hours. The crystals which have appeared are separated by filtration, washed 3 times with isopropanol (15 cc in total) cooled to a temperature of about 4° C. and 3 times with isopropyl ether (30 cc in total) and then dried under reduced pressure (20 mm Hg; 2.7 kPa) at a temperature of about 20° C. in the presence of potassium hydroxide pellets. 7-Methyl-6-(3-pyridyl)-1,2-dihydro-4H-pyrrolo[1,2-c]-1,3-thiazine-8-carbonitrile (4.8 g) is thus obtained in the form of ochre-coloured crystals melting at 166° C.

N-nicotinoyl-3,4,5,6-tetrahydro-2H-1,3-thiazine-4-carboxylic acid is prepared as described in the European Patent Application published under No. 0,118,321.

2-Chlorocrotononitrile may be prepared according to J. C. POMMELET, C. NYNS, F. LAHOUSSE, R. MERENYI and H. G. VIEHE, Angew. Chem. Int. Ed. 20, 585 (1981).

EXAMPLE 25

A solution of N-phenylpropiolamide (14 g) in acetic anhydride (60 cc) is added over 2 minutes at a temperature of about 85° C. to a solution of N-nicotinoyl-3,4,5,6-tetrahydro-2H-1,3-thiazine-4-carboxylic acid (16.2 g) in acetic anhydride (160 cc). The solution obtained is heated at a temperature of about 85° C. for 1 hour and then the solvent is evaporated off under reduced pressure (20 mm Hg; 2.7 kPa) at a temperature of about 70° C. The residual oil is suspended in a 0.4 N aqueous solution of sodium hydroxide (310 cc) and the mixture obtained is extracted 3 times with ethyl acetate (750 cc in total). The organic extracts are combined, washed twice with distilled water (400 cc in total), dried over anhydrous magnesium sulphate, treated with decolourising charcoal (0.5 g), filtered and concentrated to dryness under reduced pressure (20 mm Hg; 2.7 kPa) at a temperature of about 50° C. The product (23.5 g) thus obtained is chromatographed on a 6 cm diameter column containing silica (0.04–0.063 mm; 480 g). It is eluted with a mixture of ethyl acetate and cyclohexane (80:20 by volume) under a pressure of 0.5 bar and while 200-cc fractions are collected. The first 8 fractions are rejected. The next 6 fractions are combined, concentrated to dryness under reduced pressure (20 mm Hg; 2.7 kPa) at a temperature of about 50° C. A product (5.8 g) is obtained. The next 7 fractions are combined, concentrated to dryness under reduced pressure (20 mm Hg; 2.7 kPa) at a temperature of about 50° C. A product (4.2 g) is thus obtained, which is chromatographed again on a 6 cm diameter column containing silica (0.04–0.063 mm; 480 g). It is eluted with a mixture of ethyl acetate and cyclohexane (80:20 by volume) under a pressure of 0.5 bar and while 200-cc fractions are collected. The first 8 fractions are rejected; the following 4 fractions are combined, concentrated to dryness under reduced pressure (20 mm Hg; 2.7 kPa) at a temperature of about 50° C. A product (1.8 g) is thus obtained and is added to the 5.8 g obtained earlier and to the product (0.5 g) prepared in the same way in another operation; this single lot is taken up with boiling isopropanol (100 cc). The solution obtained is treated with decolourising charcoal (0.5 g) and filtered hot. The filtrate is cooled at a temperature of about 4° C. for 30 minutes. The crystals which have appeared are separated off by filtration, washed twice with isopropanol (20 cc in total) cooled to a temperature of about 4° C. and 3 times with isopropyl ether (60 cc in total) and then dried under reduced pressure (20 mm Hg; 2.7 kPa) at a temperature of about 20° C. in the presence of potassium hydroxide pellets. N-phenyl-6-(3-pyridyl)-1,2-dihydro-4H-pyrrolo[1,2-c]-1,3-thiazine-8-carboxamide (4.6 g) is thus obtained in the form of orange crystals melting at 160° C.

N-nicotinoyl-3,4,5,6-tetrahydro-2H-1,3-thiazine-4-carboxylic acid is prepared as described in the European Patent Application published under No. 0,118,321.

N-phenylpropiolamide may be prepared as follows:

A solution of dicyclohexylcarbodiimide (82.4 g) in anhydrous tetrahydrofuran (170 cc) is added over 20 minutes at a temperature of about 4° C. to a solution of propiolic acid (28 g) in anhydrous tetrahydrofuran (170 cc) and the suspension obtained is stirred for 30 minutes at a temperature of about 4° C. A solution of aniline (37.9 g) in anhydrous tetrahydrofuran (170 cc) is then added over 25 minutes while the same temperature is maintained and the suspension is stirred at a temperature of about 4° C. for 1 hour and then at a temperature of about 20° C. for 16 hours. The crystals are filtered off, washed 3 times with tetrahydrofuran (90 cc in total) and rejected. The filtrate is concentrated to dryness under reduced pressure (20 mm Hg; 2.7 kPa) at a temperature of about 40° C. The residual oil is dissolved in methylene chloride (350 cc), the solution obtained is washed 5 times with a N aqueous solution of hydrochloric acid (400 cc in total), 3 times with distilled water (300 cc in total), 5 times with a N aqueous solution of sodium hydroxide (400 cc in total) and 5 times with distilled water (500 cc in total), dried over anhydrous magnesium sulphate, filtered and concentrated to dryness under reduced pressure (20 mm Hg; 2.7 kPa) at a temperature of about 40° C. The product (63 g) thus obtained is chromatographed on a 5.3 cm diameter column containing silica (0.063–0.2 mm; 600 g) by eluting with methylene chloride and collecting 1-liter fractions. The first 2 fractions are rejected. The following 8 fractions are combined, concentrated to dryness under reduced pressure (20 mm Hg; 2.7 kPa) at a temperature of about 40° C. A product (24.5 g) is thus obtained and is dissolved in boiling carbon tetrachloride (75 cc). The solution obtained is cooled at a temperature of about 4° C. for 1 hour. The crystals which have appeared are separated off by filtration, washed 3 times with carbon tetrachloride (25 cc in total) cooled to a temperature of about 4° C. and are dried under reduced pressure (20 mm Hg; 2.7 kPa) at a temperature of about 20° C. in the presence of potassium hydroxide pellets. N-phenylpropiolamide (20 g) is thus obtained in the form of cream crystals melting at 86° C.

EXAMPLE 26

A solution of 3-trifluoromethylaniline (4 g) and of triethylamine (5 g) in methylene chloride (50 cc) is added over 20 minutes at a temperature of between 21° C. and 29° C. to a suspension of 7-chloroformyl-5-(3-pyridyl)-1H,3H-pyrrolo[1,2-c]thiazole hydrochloride (7.5 g) in methylene chloride (125 cc). The solution obtained is stirred at a temperature of about 20° C. for 16 hours and then methylene chloride (200 cc) and distilled water 150 cc) are added to it. The organic phase is separated off, washed twice with distilled water (300 cc in total), dried over anhydrous magnesium sulphate, treated with decolourising charcoal (0.5 g), filtered and concentrated to dryness under reduced pressure (20 mm Hg; 2.7 kPa) at a temperature of about 50°

C. A product (5.6 g) melting at 190° C. is thus obtained. This product is dissolved in boiling ethanol (160 cc); the solution obtained is treated with decolourising charcoal (0.5 g) and filtered hot. The filtrate is cooled at a temperature of about 4° C. for 2 hours. The crystals which have appeared are separated off by filtration, washed twice with ethanol (50 cc in total) and 3 times with diethyl ether (75 cc in total) and then dried under reduced pressure (20 mm Hg; 2.7 kPa) at a temperature of about 20° C. in the presence of potassium hydroxide pellets. N-(3-trifluoromethyl- phenyl)-5-(3-pyridyl)-1H,3H-pyrrolo[1,2-c]thiazole-7-carboxamide (2.9 g) is thus obtained in the form of pale yellow crystals melting at 198° C.

7-Chloroformyl-5-(3-pyridyl)-1H,3H-pyrrolo[1,2-c]thiazole hydrochloride is prepared as in Example 1.

EXAMPLE 27

A solution of 2-hydroxy-5-(3-pyridyl)-2,3-dihydro-1H-pyrrolizine-7-carbonitrile (4.7 g) in a 12 N aqueous solution of hydrochloric acid (110 cc) is heated at a temperature of about 80° C. for 2 hours and is then concentrated to dryness under reduced pressure (20 mm Hg; 2.7 kPa) at a temperature of about 60° C. A product (8 g) is thus obtained, and is dissolved in distilled water (20 cc). The resulting solution is adjusted to a pH of about 8 by addition of a 1.19 N saturated aqueous solution of sodium hydrogen carbonate (100 cc) and is then concentrated to dryness under reduced pressure (20 mm Hg; 2.7 kPa) at a temperature of about 60° C. The solid obtained is taken up for a first time with a mixture (500 cc) of methylene chloride and methanol (80:20 by volume). A solution and an insoluble material are thus obtained. The solution is carefully decanted and poured into a 13 cm diameter column containing silica (0.063-0.2 mm; 400 g). The insoluble material is again taken up with a mixture (500 cc) of methylene chloride and methanol (80:20 by volume) and treated as before. The operation is thus restarted 9 times in succession. The organic solutions which are collected at the bottom of the column are combined and concentrated to dryness under reduced pressure (20 mm Hg; 2.7 kPa) at a temperature of about 60° C. A product (4.7 g) is thus obtained, which is combined with a product (0.5 g) prepared in the same way in another operation and dissolved in boiling ethanol (140 cc). The solution obtained is treated with decolourising charcoal (0.5 g) and filtered hot. The filtrate is cooled at a temperature of about 4° C. for 16 hours. The crystals which have appeared are separated off by filtration, washed twice with ethanol (50 cc in total) and 3 times with diethyl ether (75 cc in total) and then dried under reduced pressure (20 mm Hg; 2.7 kPa) at a temperature of about 20° C. in the presence of potassium hydroxide pellets. 2-Hydroxy-5-(3-pyridyl)-2,3-dihydro-1H-pyrrolizine-7-carboxamide (3.3 g) is thus obtained in the form of cream crystals melting at 206° C.

2-Hydroxy-5-(3-pyridyl)-2,3-dihydro-1H-pyrrolizine-7-carbonitrile may be prepared as follows:

A suspension of N-nicotinoyl-4-hydroxyproline (34 g) in a mixture of 2-chloroacrylonitrile (115 cc) and of acetic anhydride (150 cc) is heated at a temperature of about 90° C. for 3 hours and 40 minutes. The solution obtained is concentrated to dryness under reduced pressure (20 mm Hg; 2.7 kPa) at a temperature of about 70° C. The residue obtained is suspended in a 5 N aqueous solution of sodium hydroxide (500 cc) and the resulting suspension is extracted 4 times with ethyl acetate (1,250 cc in total). The organic extracts are combined, washed 4 times with distilled water (1,000 cc in total), dried over anhydrous magnesium sulphate, treated with decolourising charcoal (0.5 g), filtered and concentrated to dryness under reduced pressure (20 mm Hg; 2.7 kPa) at a temperature of about 60° C. A crude product (13 g) is thus obtained, which is dissolved in boiling isopropanol (130 cc). The solution obtained is filtered hot and the filtrate is cooled at a temperature of about 20° C. for 2 hours. The crystals which have appeared are separated off by filtration, washed twice with isopropanol (50 cc in total) and 3 times with diethyl ether (150 cc in total), and then dried under reduced pressure (20 mm Hg; 2.7 kPa) at a temperature of about 20° C. in the presence of potassium hydroxide pellets. 2-Hydroxy-5-(3-pyridyl)-2,3-dihydro-1H-pyrrolizine-7-carbonitrile (5.6 g) is thus obtained in the form of beige crystals melting at 190° C.

N-nicotinoyl-4-hydroxyproline may be prepared as follows:

A 5 N aqueous solution of sodium hydroxide (346 cc) is added over 25 minutes at a temperature of between 14° C. and 26° C. to a suspension of ethyl bis-0,N-nicotinoyl-4-hydroxyprolinate (212.8 g) in ethanol (2,130 cc). The solution obtained is stirred at a temperature of about 20° C. for 16 hours and is then adjusted to a pH of about 3 by addition of a 12 N aqueous solution of hydrochloric acid (160 cc). The crystals which have appeared are removed by filtration and the filtrate is concentrated to dryness under reduced pressure (20 mm Hg; 2.7 kPa) at a temperature of about 70° C. The residue obtained is suspended in boiling ethanol (1,250 cc). After cooling to a temperature of about 20° C., the crystals are removed by filtration and the filtrate is concentrated to half its volume under reduced pressure (20 mm Hg; 2.7 kPa) at a temperature of about 50° C. The solution obtained is cooled at a temperature of about 4° C. for 16 hours. The crystals which have appeared are separated off by filtration, washed 3 times with ethanol (300 cc in total) and 3 times with diethyl ether (450 cc in total) and then dried under reduced pressure (20 mm Hg; 2.7 kPa) at a temperature of about 20° C. in the presence of potassium hydroxide pellets. N-nicotinoyl-4-hydroxyproline (112.6 g) is thus obtained in the form of pale pink crystals melting at 172° C.

Bis-O,N-nicotinoyl-4-hydroxyproline may be prepared as follows:

Triethylamine (655 g) is added over 10 minutes to a suspension of ethyl 4-hydroxyprolinate hydrochloride (209.6 g) in methylene chloride (2,800 cc), while the temperature is kept at about 24° C. During this time, a transient formation of a clear homogeneous phase is noted after 5 minutes, followed immediately by a precipitation. Nicotinoyl chloride hydrochloride (480.6 g) is added over 15 minutes to the suspension obtained, at a temperature of between 23° C. and 43° C. The suspension obtained is heated at a temperature of about 43° C. for 3 hours and is then stirred at a temperature of about 20° C. for 16 hours. Methylene chloride (1,000 cc) and water (2,000 cc) are then added to the suspension. The organic phase is separated off, washed 3 times with distilled water (3,000 cc in total), dried over anhydrous magnesium sulphate, treated with decolourising charcoal (0.5 g), filtered and concentrated to dryness under reduced pressure (20 mm Hg; 2.7 kPa) at a temperature of about 60° C. A crude product (458.7 g) melting at 80° C. is thus obtained. This product is taken up with boiling distilled water (2,000 cc). The insoluble oil which has appeared is separated off hot and the aqueous phase is filtered hot. The filtrate is cooled at a temperature of about 4° C. for 16 hours. The crystals which have appeared are separated off by filtration, washed 3 times with distilled water (750 cc in total) and dried in air. Ethyl bis-O,N-nico- tinoyl-4-hydroxyprolinate (212.8 g) is thus obtained in the form of pale yellow crystals melting at 110° C.

Ethyl 4-hydroxyprolinate hydrochloride may be prepared according to J. KAPFHAMMER and A. MATTHES, Z. Physiol. Chem., 223, 48 (1934).

EXAMPLE 28

A solution of 3-methoxyaniline (3.1 g) and of triethylamine (5.1 g) in methylene chloride (50 cc) is added over 15 minutes at a temperature of between 21° and 28° C. to a suspension of 7-chloroformyl-5-(3-pyridyl)-1H,3H-pyrrolo[1,2-c]thiazole hydrochloride (7.5 g) in methylene chloride (125 cc). The solution obtained is stirred at a temperature of about 20° C. for 16 hours. A product precipitates out. The crystals which have appeared are separated off by filtration, washed 3 times with methylene chloride (300 cc in total) and 3 times with distilled water (300 cc in total) and then dried under reduced pressure (20 mm Hg; 2.7 kPa) at a temperature of about 20° C. in the presence of potassium hydroxide pellets. A crude product (5.1 g) melting at 220° C. is thus obtained. This product is dissolved in boiling 1-butanol (160 cc). The cloudy solution obtained is treated with decolourising charcoal (0.5 g) and filtered hot. The filtrate is cooled at a temperature of about 4° C. for 16 hours. The crystals which have appeared are separated off by filtration, washed twice with 1-butanol (30 cc in total) 3 times with ethanol (75 cc in total) and 3 times with diethyl ether (75 cc in total) and then dried under reduced pressure (20 mm Hg; 2.7 kPa) at a temperature of about 20° C. in the presence of potassium hydroxide pellets. N-(3-Methoxyphenyl)-5-(3-pyridyl)-1H,3H-pyrrolo[1,2-c]thiazole-7-carboxamide (3.9 g) is thus obtained in the form of pale yellow crystals melting at 224° C.

7-Chloroformyl-5-(3-pyridyl)-1H,3H-pyrrolo[1,2-c]thiazole hydrochloride is prepared as in Example 1.

EXAMPLE 29

A suspension of a mixture (in a proportion of 10:90; 6 g) of 6-cyano and 7-cyano-5-(3-pyridyl)-2,3-dihydropyrrolo[2,1-b]thiazole hydrochloride and of potassium hydroxide powder (7.5 g) in tert-butyl alcohol (140 cc) is heated at a temperature of about 82° C. for 1 hour and 10 minutes. The reaction mixture is concentrated to dryness under reduced pressure (20 mm Hg; 2.7 kPa) at a temperature of about 50° C. and the residue obtained is suspended in distilled water (100 cc). The crystals which have appeared are separated off by filtration, washed 5 times with distilled water (200 cc in total) and 3 times with ethanol (30 cc in total) and then dried under reduced pressure (20 mm Hg; 2.7 kPa) at a temperature of about 20° C. A crude product (3 g) melting at 251° C. is thus obtained. A product prepared in the same way during another operation (1.4 g) is added to this product and the single lot obtained is dissolved in dimethylformamide (37 cc) heated to a temperature of about 125° C. The solution obtained is treated with decolourising charcoal (0.5 g) and filtered hot. The filtrate is cooled at a temperature of about 4° C. for 1 hour. The crystals which have appeared are separated off by filtration, washed 3 times with dimethylformamide (3 cc in total) cooled to a temperature of about 4° C., 5 times with ethanol (15 cc in total) cooled at a temperature of about 4° C. and 5 times with diethyl ether (25 cc in total) and then dried under reduced pressure (20 mm Hg; 2.7 kPa) at a temperature of about 20° C. in the presence of potassium hydroxide pellets. 5-(3-Pyridyl)-2,3-dihydropyrrolo[2,1-b]thiazole-7-carboxamide (3 g) is thus obtained in the form of cream crystals melting at 253° C.

The mixture (in the proportion of 10:90) of 6-cyano and 7-cyano-5-(3-pyridyl)-2,3-dihydropyrrolo[2,1-b]thiazole hydrochloride may be prepared as follows:

A suspension of N-nicotinoylthiazolidine-2-carboxylic acid (9.5 g) and of 2-chloroacrylonitrile (35 g) in acetic anhydride (100 cc) is heated at a temperature of between 88° C. and 108° C. for 2 hours. During this period, a transient formation of a clear homogeneous phase is noted after 30 minutes, followed by precipitation 25 minutes later. After cooling at a temperature of about 20° C. for 16 hours, the crystals which have appeared are separated off by filtration, washed twice with acetic anhydride (10 cc in total) and twice with diethyl ether (20 cc in total) and then dried under reduced pressure (20 mm Hg; 2.7 kPa) at a temperature of about 20° C. in the presence of potassium hydroxide pellets. A mixture (8.6 g) of 6-cyano and 7-cyano-5-(3-pyridyl)-2,3-dihydropyrrolo[2,1-b]thiazole hydrochloride is thus obtained in the form of reddish brown crystals melting at 160° C., in a proportion of 10:90 (according to the NMR spectrum).

N-nicotinoylthiazolidine-2-carboxylic acid may be prepared as follows:

Triethylamine (133.6 g) is added over 5 minutes at a temperature of between 22° and 30° C. to a suspension of thiazolidine-2-carboxylic acid (77 g) in chloroform (700 cc). Nicotinoyl chloride hydrochloride (117.5 g) is added over 1 hour, at a temperature of between 23° and 40° C., to the solution obtained. The solution obtained is heated at a temperature of about 64° C. for 2 hours. After cooling at a temperature of about 20° C. for 16 hours and then at a temperature of about 4° C. for 1 hour, the crystals which have appeared are separated off by filtration, washed 3 times with chloroform (300 cc in total) cooled at a temperature of about 4° C. and rejected. The filtrate is concentrated to dryness under reduced pressure (20 mm Hg; 2.7 kPa) at a temperature of about 65° C. The residue is suspended in acetone (1,000 cc) and the crystals which have appeared are separated by filtration, washed 3 times with acetone (750 cc in total) and rejected. The filtrate is concentrated to dryness under reduced pressure (20 mm Hg; 2.7 kPa) at a temperature of about 60° C. A product (150 g) is obtained. This product is dissolved in distilled water (500 cc) and the solution is adjusted to a pH of about 9 by addition of a 10 N aqueous solution of sodium hydroxide; the solution is poured into a 6 cm diameter column containing DOWEX 50 W X 2 resin in H+ form (50–100 mesh; 1 kg). The material is eluted with distilled water, 1,000-cc fractions being collected. The first two fractions are rejected. The following four fractions are combined and concentrated to a volume of 150 cc under reduced pressure (20 mm Hg; 2.7 kPa) at a temperature of about 60° C. The solution obtained is left at a temperature of about 20° C. for 16 hours. A product precipitates out. The crystals which have appeared are separated off by filtration, washed twice with distilled water (10 cc in total), twice with ethanol (10 cc in total) and are dried under reduced pressure (20 mm Hg; 2.7 kPa) at a temperature of about 20° C. in the presence of potassium hydroxide pellets. N-nicotinoyl-thiazolidine-2-carboxylic acid (9.5 g) is thus obtained in the form of white crystals melting at 180 C.

Thiazolidine-2-carboxylic acid may be prepared according to R. L. JOHNSON, E. E. SMISSMAN and N. P. PLOTNIKOFF, J. Med. Chem. 21, 165 (1978).

EXAMPLE 30

A solution of cyclohexylamine (11.9 g) in methylene chloride (50 cc) is added over 15 minutes, at a temperature of between 20° and 31° C., to a suspension pf 7-chloroformyl-5-(3-pyridyl)-1H,3H-pyrrolo[1,2-c]thiazole hydrochloride (12 g) in methylene chloride (200 cc). The solution obtained is stirred at a temperature of about 20° C. for 16 hours and then methylene chloride (250 cc) and distilled water (250 cc) are added to it. The organic phase is separated off, washed 3 times with distilled water (750 cc in total), dried over anhydrous magnesium sulphate, treated with decolourising charcoal (0.5 g), filtered and concentrated to dryness under reduced pressure (20 mm Hg; 2.7 kPa) at a temperature of about 60° C. A product (13.1 g) melting at 180° C. is thus obtained, and is dissolved in boiling ethanol (200 cc). The solution obtained is treated with decolourising charcoal (0.5 g) and filtered hot. The filtrate is cooled at a temperature of about 4° C. for 1 hour. The crystals which have appeared are separated off by filtration, washed twice with ethanol (50 cc in total) cooled to a temperature of about 4° C. and 3 times with diethyl ether (75 cc in total) and then dried under reduced pressure (20 mm Hg; 2.7 kPa) at a temperature of about 20° C. in the presence of potassium hydroxide pellets. N-Cyclohexyl-5-(3-pyridyl)-1H,3H-pyrrolo[1,2-c]-thiazole-7-carboxamide (4.5 g) is thus obtained in the form of beige crystals melting at 188° C.

7-Chloroformyl-5-(3-pyridyl)-1H,3H-pyrrolo[1,2-c]thiazole hydrochloride is prepared as in Example 1.

The present invention also relates to medicaments consisting of a product of general formula (I) in free form or in the form of a salt of addition with a pharmaceutically acceptable acid, in the pure state or in the form of a composition in which it is combined with any other pharmaceutically compatible product, which may be inert or active physiologically. The medicaments according to the invention may be employed by oral, parenteral, rectal or topical routes.

As solid compositions for oral administration, use may be made of tablets, pills, powders (particularly in gelatin capsules or cachets) or granules. In these compositions, the active product according to the invention is mixed with one or more inert diluents such as starch, cellulose, sucrose, lactose or silica. These compositions may also contain substances other than diluents, for example one or more lubricants such as magnesium stearate or talc, a colorant, a coating (coated tablets) or a varnish.

As liquid compositions for oral administration, use may be made of solutions, suspensions, emulsions, syrups and pharmaceutically acceptable elixirs containing inert diluents such as water, ethanol, glycerol, vegetable oils or paraffin oils. These compositions may contain substances other than diluents, for example wetting agents, sweeteners, thickeners, flavourings or stabilisers.

The sterile compositions for parenteral administration may preferably be aqueous or non-aqueous solutions, suspensions or emulsions. Use may be made, as a solvent or vehicle, of water, propylene glycol, polyethylene glycol, vegetable oils in particular olive oil, injectable organic esters, for example ethyl oleate or other suitable organic solvents. These compositions may also contain adjuvants, in particular wetting agents, isotonising agents, emulsifiers, dispersants and stabilisers. The sterilisation may be carried out in various ways, for example by asepticising filtration, by incorporating sterilising agents in the composition, by irradiation or by heating. They may also be prepared in the form of sterile solid compositions which may be dissolved at the time of use in an injectable sterile medium.

The compositions for rectal administration are suppositories or rectal capsules which, in addition to the active product, contain excipients such as cocoa butter, semi-synthetic glycerides or polyethylene glycols.

The compositions for topical administration may be, for example, creams, pomades, lotions, eye lotions, mouth washes, nasal drops or aerosols.

In human therapeutics, the products according to the invention are particularly useful in the prophylactic and therapeutic treatment of thrombotic complaints. The dosages depend on the required effect and on the duration of the treatment, they are generally between 100 and 1,000 mg per day for oral administration in one or more doses for an adult, and between 10 and 100 mg by parenteral administration in one or more injections for an adult.

In general, the practitioner will determine the dosage which is considered the most suitable as a function of age, weight and all the other factors peculiar to the subject to be treated.

The following examples, given without implying a limitation, illustrate the compositions according to the invention.

EXAMPLE A

Tablets containing 200-mg doses of the active product and having the following composition are prepared according to the usual technique:

N-(1-adamantyl)-5-(3-pyridyl)-1H,3H-pyrrolo[1,2-c]thiazole-7-carboxamide: 200 mg
starch: 60 mg
lactose: 50 mg
magnesium stearate: 2 mg

EXAMPLE B

Tablets containing 200-mg doses of the active product and having the following composition are prepared according to the usual technique:

N-(3-chlorophenyl)-5-(3-pyridyl)-1H,3H-pyrrolo[1,2-c]thiazole-7-carboxamide: 200 mg
starch: 60 mg
lactose: 50 mg
magnesium stearate: 2 mg

EXAMPLE C

An injectable solution containing 20 mg of active product and having the following composition is prepared:

N-(3-pyridyl)-5-(3-pyridyl)-1H,3H-pyrrolo[1,2-c]thiazole-7-carboxamide: 20 mg
0.1 N methanesulphonic acid: 0.62 cc
injectable solution q.s.: 2 cc

We claim:

1. An ortho-condensed pyrrole derivative, of the formula:

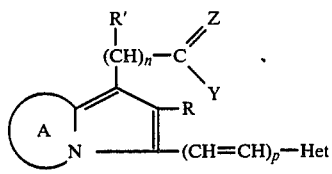

in which R' denotes a hydrogen atom or an alkyl or phenyl radical which unsubstituted or substituted by halogen, alkyl, alkyloxy or alkylthio;

Z denotes an oxygen or sulphur atom; p denotes zero or 1; and (A) either the symbol A denotes a heterocyclic ring which, with the pyrrole nucleus with which it is condensed, forms a ring system selected from 1H,3H-pyrrole[1,2-c]thiazole, 1,2-dihydro-4H-pyrrolo[1,2-c]-1,3-thiazine, and 2,3dihydropyrrolo[2,1-b]thiazole; n denotes 0 or 1;

Het denotes 3-pyridyl;

and (1) either R denotes hydrogen or halogen or an alkyl or phenyl radical which is unsubstituted or substituted by halogen, alkyl, alkyloxy or alkylthio, and Y denotes an alkyl or phenyl radical which is unsubstituted or substituted by halogen, alkyl, alkyloxy or alkylthio, or Y denotes a radical of formula:

in which either $R_1$ denotes a hydrogen atom and $R_2$ denotes an unsubstituted alkyl radical, a cycloalkyl radical of 3 to 6 carbon atoms, an alkenyl radical of 2 to 4 carbon atoms, an alkynyl radical of 3 or 4 carbon atoms, or a benzyl or phenyl radical which is unsubstituted or substituted by halogen, alkyl, alkyloxy, alkylthio, trifluoromethyl or nitro, or $R_2$ denotes an adamantyl, radical, or $R_1$ and $R_2$ both denote an unsubstituted alkyl radical;

(2) or R denotes halogen or an alkyl or phenyl radical which is unsubstitued or substituted by halogen, alkyl, alkyloxy or alkylthio, and Y denotes an amino radical;

(B) or the symbol A denotes a heterocyclic ring which, with the pyrrole nucleus with which it is condensed, forms a 2,3-dihydropyrrolo[2,1-b]thiazole ring;

R denotes a hydrogen atom;
Y denotes an amino radical, n denotes zero or 1;
and Het denotes 3-pyridyl;

(C) or the symbol A denotes a heterocyclic ring which, with the pyrrole nucleus with which it is condensed, forms a ring system selected from 1H,3H-pyrrole[1,2-c]thiazole, and 1,2-dihydro-4H-pyrrolo[1,2-c]-1,3-thiazine;

R denotes a hydrogen atom,
Y denotes an amino radical;
and Het denotes 3-pyridyl arid n is 1;

it being understood that, unless specifically mentioned, the aforesaid alkyl radicals and alkyl portions contain 1 to 4 carbon atoms each and are straight-chain or branched-chain; and its acid addition salts.

2. A pyrrole derivative as claimed in claim 1 in which R' denotes a hydrogen atom, Z denotes an oxygen atom, p is equal to zero and A. either the symbol A denotes a heterocyclic ring such that, with the pvrrole nucleus with which it is condensed, it forms a 1H,3H-pyrrole[1,2-c]thiazole or 1,2-dihydro4H-pyrrolo[1,2-c]-1,3-thiazine ring system, n is equal to zero, Het denotes a 3-pyridyl radical and (1) either R denotes a hydoogen atom and Y denotes an alkyl or phenyl radical, or y denotes a radical of general formula (II) in which:

either $R_1$ denotes a hydrogen atom and $R_2$ denotes an unsubstituted alkyl radical. a cycloalkyl radical containing 3 to 6 carbon atoms, an alkenyl radical containing 2 to 4 carbon atoms, benzyl or phenyl radicals optionally substituted by a halogen atom or an alkyloxy or trifluoromethyl radical, or $R_2$ denotes an adamantyl, radical or $R_1$ and $R_2$ both denote an unsubstituted alkyl radical (2) or R denotes a halogen atom or an alkyl radical, and Y denotes an amino radical, B. or the symbol A denotes a heterocyclic ring such that, with the pyrrole nucleus with which it is condensed, it forms a 2,3-dihydropyrrolo[2,1-b]thiazole ring system, R denotes a hydrogen atom, Y denotes an amino radical, n is equal to zero and Het denotes a 3-pyridyl radical, C. or the symbol A denotes a heterocyclic ring such that, with the pyrrole nucleus with which it is condensed, it forms a 1H,3H-pyrrolo[1,2-c]thiazole ring system, R denotes a hydrogen atom, Y denotes an amino radical and Het denotes a 3-pyridyl radical and n is equal to 1.

3. A pyrrole derivative as claimed in claim 1 in which R' denotes a hydrogen atom, Z denotes ao oxygen atom, p is equal to zero and A. either the symbol A denotes a heterocyclic ring such that with the pyrrole nuoleus with which it is condensed, it forms a 1H,3H-pyrrolo[1,2-c]thiazole, or 1,2-dihydro-4H-pyrrolo[1,2-c]-1,3-thiazine ring system, n is equal to zero, Het denotes a 3-pyridyl radical and (1) either R denotes a hydrogen atom and Y denotes a phenyl radical, or Y denotes a radical of general formula (II) in which $R_1$ denotes a hydrogen atom and $R_2$ denotes an unsubstituted alkyl radical, benzyl or phenyl radicals optionally substituted by a haloqen atom or an alkyloxy radical, or $R_2$ denotes an adamantyl radical, (2) or R denotes a halogen atom or an alkyl radical, and Y denotes an amino radical, B. or the symbol A denotes a heterocyclic ring such that, with the pyrrole nucleus with which it is condensed it forms a 2,3-dihydropyrrolo[2,1]-thiazole ring system, R denotes a hydrogen atom, Y denotes an amino radical, n is equal to zero and Het denotes a 3-pyridyl radical.

4. A pyrrole derivative as claimed in claim 1 which is -N-(1-adamantyl)-5-(3-pyridyl)-1H,3H-pyrrolo-[1,2-c]thiazole-7-carboxamide and its acid addition salts.

5. A pyrrole derivative as claimed in claim 1 which is N-(3-chlorophenyl)-5-(3-pyridyl)-1H,3M-pyrrolo[1,2c]-thiazole 7-carboxamide and its acid addition salts.

6. A pyrrole derivative as claimed in claim 1 which is 7-benzoyl-5-(3-pyridyl)-1H,3H-pyrrolo[1,2-c]thiazole and acid addition salts.

7. A pyrrole derivative as claimed in claim 1 which is N-isopropyl-5-(3-pyridyl)-1H,3H-pyrrolo[1,2-c]thiazole-7-carboxamide and its acid addition salts.

8. A pyrrole derivative as claimed in claim 1 which is N-benzyl-5-(3-pyridyl)-1H,3H-pyrrolo[1,2-c]thiazole-7-carboxamide and its acid addition salts.

9. A pyrrole derivative as claimed in claim 1 which is 6-bromo-5-(3-pyridyl)-1H,3H-pyrrolo-[1,2-c]thiazole-7carboxamide and its acid addition salts.

10. A pyrrole derivative as claimed in claim 1 which is N-methyl-5-(3-pyridyl)-1,2-dihydro-4H-pyrrolo[1,2-c]-1,3-thiazine-8-carboxamide and its acid addition salts.

11. A pyrrole derivative as claimed io claim 1 which is 7-methyl-6-(3-pyridyl)-1,2-dihydro-4H-pyrrolo[1,2-c]-1,3-thiazine-8-carboxamide and its acid addition salts.

12. A pyrrole derivative as claimed in claim 1 which is N-phenyl-6-(3-pyridyl)-1,2-dihydro-4H-pyrrolo[1,2-c]-1,3-thiazine-8-carboxamide and its acid addition salts.

13. A pyrrole derivative as claimed in claim 1 which is N-(3-methoxyphenyl)-5-(3-pyridyl)-1H,3H-pyrrolo[1,2-c]-thiazole-7-carboxamide aod its acid addition salts.

14. A pyrrole derivative as claimed in claim 1 which is 5-(3-pyridyl)-2,3-dihydropyrrolo[2,1]thiazole-7-carboxamide and its acid addition salts.

15. A pyrrole derivative as claimed in claim 1 which is N-methyl-5-(3-pyridyl)-1H,3H-pyrrolo[1,2-c]thiazole-7-carboxamide and its acid addition salts.

16. An anti-thrombotic pharmaceutical composition comprising an anti-thrombotic effective amount of a pyrrole derivative as claimed in claim 1 in association with a compatible, pharmaceutically acceptable diluent or adjuvant.

17. Method for the treatment or prophylaxis of thrombosis which comprises administering to a subject in which such therapy is required an anti-thrombotic effective amount of a pyrrole derivative as claimed in claim 1.

* * * * *